United States Patent
Singhatat et al.

(10) Patent No.: US 8,979,873 B2
(45) Date of Patent: Mar. 17, 2015

(54) MULTI-STITCH ANCHOR SUTURE-BASED SOFT TISSUE REPAIR SYSTEM

(75) Inventors: Wamis Singhatat, West Chester, PA (US); Jamie Manos, West Chester, PA (US)

(73) Assignee: DePuy Synthes Products, LLC, Raynham, MA (US)

(*) Notice: Subject to any disclaimer, the term of this patent is extended or adjusted under 35 U.S.C. 154(b) by 451 days.

(21) Appl. No.: 12/887,601

(22) Filed: Sep. 22, 2010

(65) Prior Publication Data

US 2011/0071551 A1 Mar. 24, 2011

Related U.S. Application Data

(60) Provisional application No. 61/244,504, filed on Sep. 22, 2009.

(51) Int. Cl.
*A61B 17/10* (2006.01)
*A61B 17/04* (2006.01)
*A61B 17/00* (2006.01)

(52) U.S. Cl.
CPC ... *A61B 17/0401* (2013.01); *A61B 2017/00867* (2013.01); *A61B 2017/0409* (2013.01); *A61B 2017/0417* (2013.01); *A61B 2017/0443* (2013.01); *A61B 2017/0456* (2013.01)
USPC .......................................... 606/139; 606/232

(58) Field of Classification Search
USPC ......... 606/139, 144, 145, 148, 215, 222, 224, 606/228, 232, 233, 916; 206/63.3, 339
See application file for complete search history.

(56) References Cited

U.S. PATENT DOCUMENTS

| 1,822,330 | A |   | 9/1931 | George |
|---|---|---|---|---|
| 2,738,790 | A |   | 3/1956 | Todt et al. |
| 4,010,737 | A | * | 3/1977 | Vilaghy et al. ................ 600/567 |
| 5,059,201 | A |   | 10/1991 | Asnis |
| 5,312,423 | A |   | 5/1994 | Rosenbluth et al. |

(Continued)

FOREIGN PATENT DOCUMENTS

| EP | 1484021 | 12/2004 |
|---|---|---|
| EP | 1938760 | 7/2008 |

(Continued)

OTHER PUBLICATIONS

International Patent Application No. PCT/US2010/049788: International Search Report dated Feb. 2, 2011, 5 pages.

(Continued)

*Primary Examiner* — Elizabeth Houston
*Assistant Examiner* — Robert Lynch
(74) *Attorney, Agent, or Firm* — Baker & Hostetler LLP

(57) ABSTRACT

A soft tissue repair system includes a needle, a sheath, and a actuator. The needle has a body and a tip that extends distally from the body. The body defines a longitudinal channel configured to hold a plurality of suture anchors, and an ejection port proximal to the tip. The needle is configured to receive and hold a strand of suture. The sheath is disposed coaxially around the exterior of the needle, and is translatable with respect to the needle between a first position, and a second position. The actuator is translatable within the needle channel and is configured to push the suture anchors distally such that a first suture anchor of the plurality of suture anchors engages the suture strand held by the needle and sheath.

29 Claims, 17 Drawing Sheets

(56) References Cited

U.S. PATENT DOCUMENTS

| | | | |
|---|---|---|---|
| 5,746,752 | A | 5/1998 | Burkhart |
| 5,792,151 | A | 8/1998 | Heck et al. |
| 5,816,258 | A | 10/1998 | Jervis |
| 5,868,762 | A | 2/1999 | Cragg et al. |
| 6,221,084 | B1 | 4/2001 | Fleenor |
| 6,245,079 | B1 | 6/2001 | Nobles et al. |
| 6,443,963 | B1 | 9/2002 | Baldwin et al. |
| 6,551,330 | B1 | 4/2003 | Bain et al. |
| 6,562,052 | B2 | 5/2003 | Nobles et al. |
| 6,770,084 | B1 | 8/2004 | Bain et al. |
| 6,893,448 | B2 | 5/2005 | O'Quinn et al. |
| 6,936,054 | B2 | 8/2005 | Chu |
| 7,118,583 | B2 | 10/2006 | O'Quinn et al. |
| 7,815,654 | B2 | 10/2010 | Chu |
| 8,608,758 | B2 | 12/2013 | Singhatat et al. |
| 2002/0045908 | A1 | 4/2002 | Nobles et al. |
| 2002/0156344 | A1 | 10/2002 | Pasricha et al. |
| 2003/0225361 | A1* | 12/2003 | Sabra .............. 604/19 |
| 2005/0154402 | A1 | 7/2005 | Sauer et al. |
| 2006/0184203 | A1* | 8/2006 | Martin et al. ............ 606/232 |
| 2008/0065156 | A1 | 3/2008 | Hauser et al. |
| 2008/0243148 | A1* | 10/2008 | Mikkaichi et al. .......... 606/144 |
| 2009/0048613 | A1* | 2/2009 | Surti .............. 606/139 |
| 2009/0082786 | A1* | 3/2009 | Surti .............. 606/139 |
| 2010/0049212 | A1 | 2/2010 | Carborn et al. |

FOREIGN PATENT DOCUMENTS

| | | |
|---|---|---|
| WO | WO 99/25254 | 5/1999 |
| WO | WO 02/22026 | 3/2002 |
| WO | WO 2006/086275 | 8/2006 |
| WO | WO 2011/037977 | 3/2011 |

OTHER PUBLICATIONS

U.S. Appl. No. 12/693,820, filed Jan. 26, 2010, Adams.

* cited by examiner

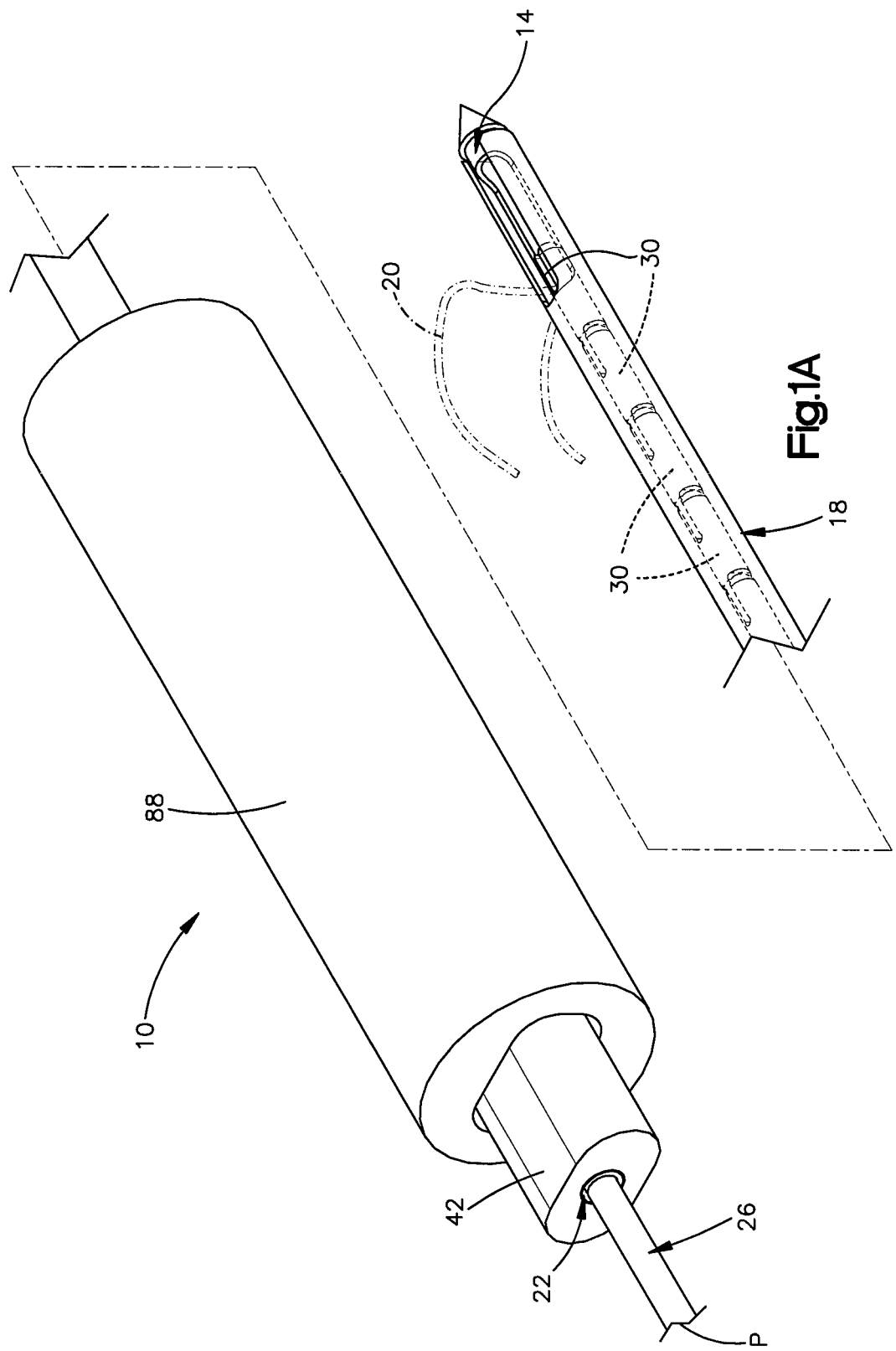

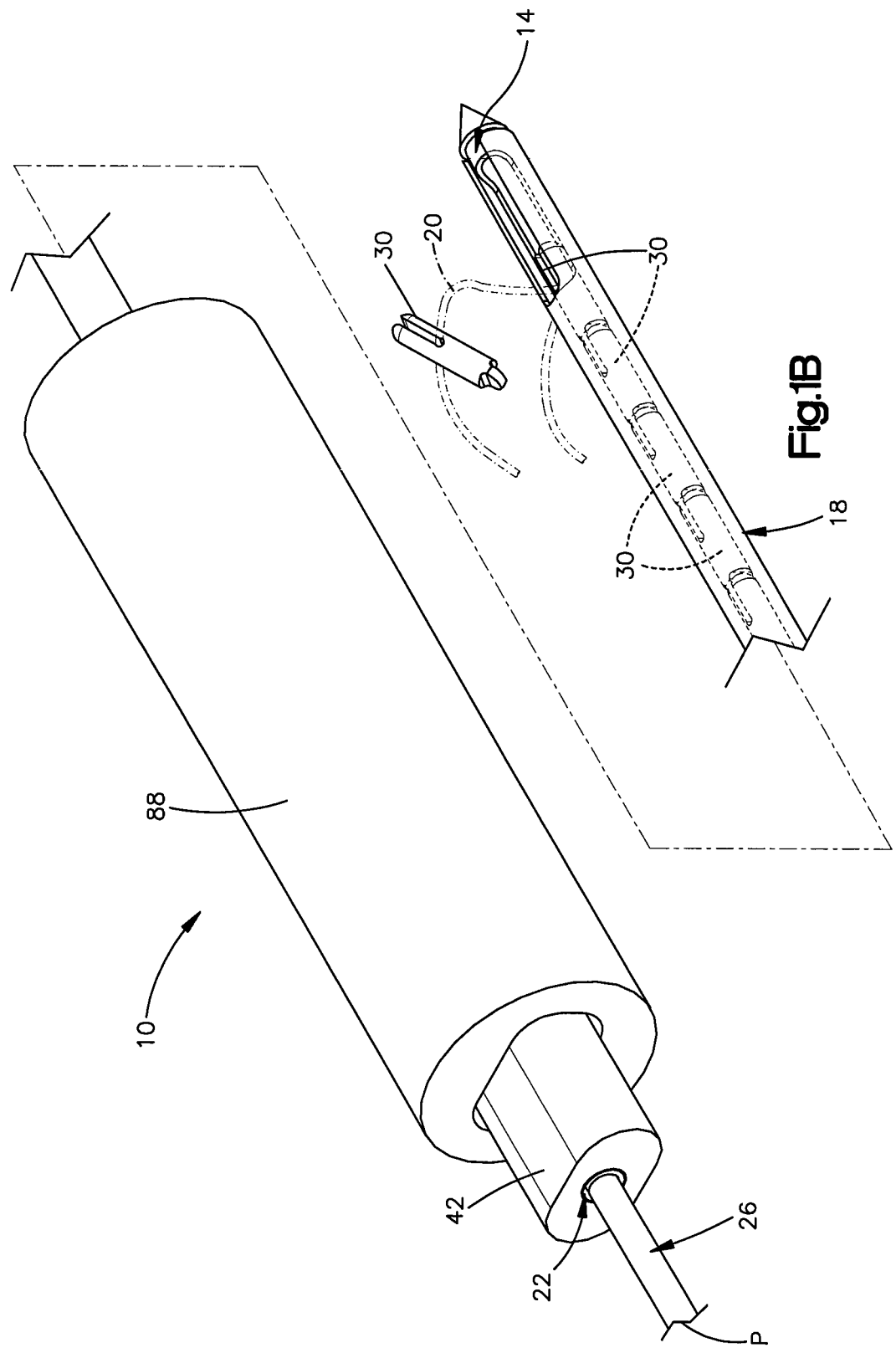

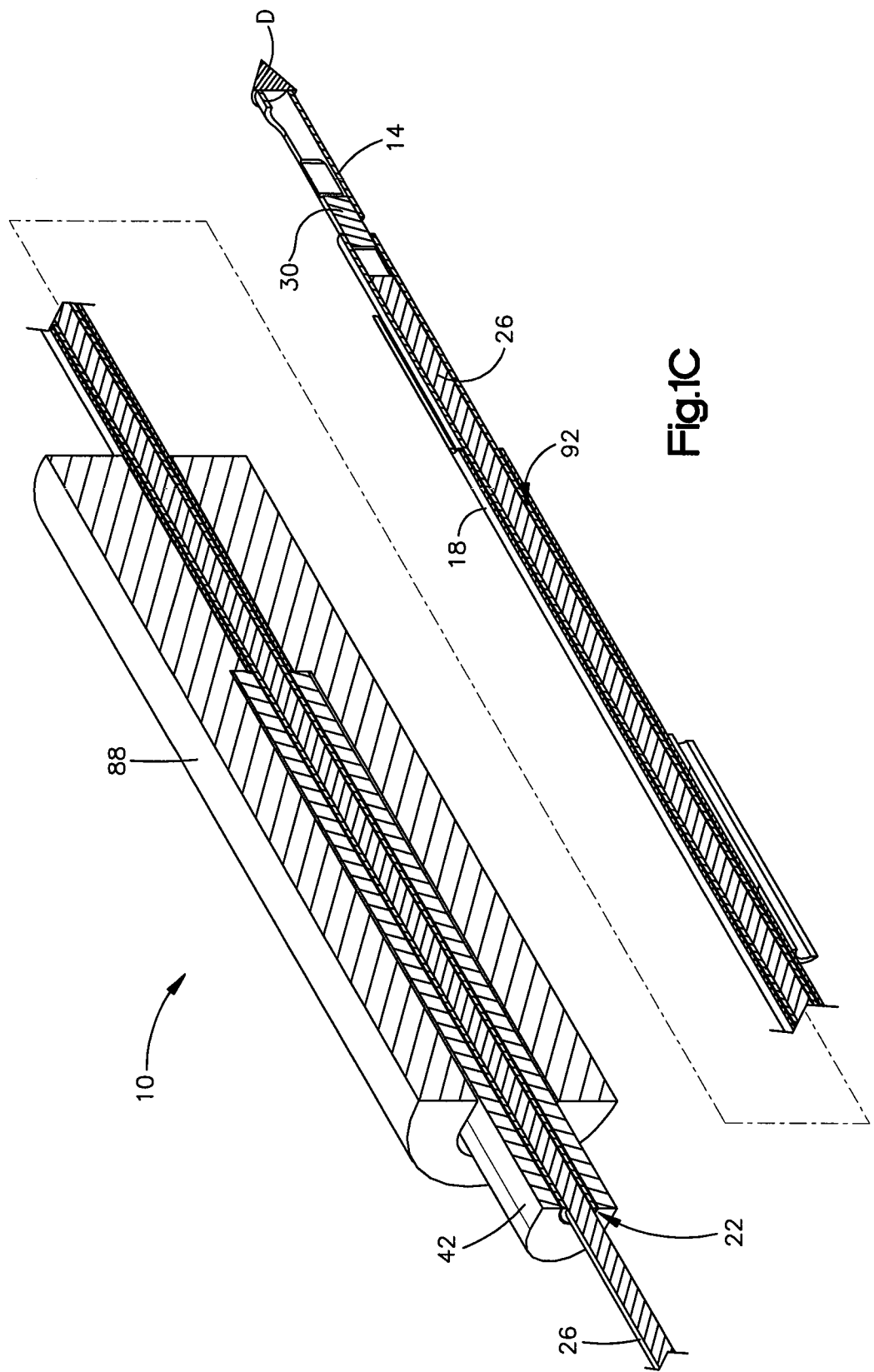

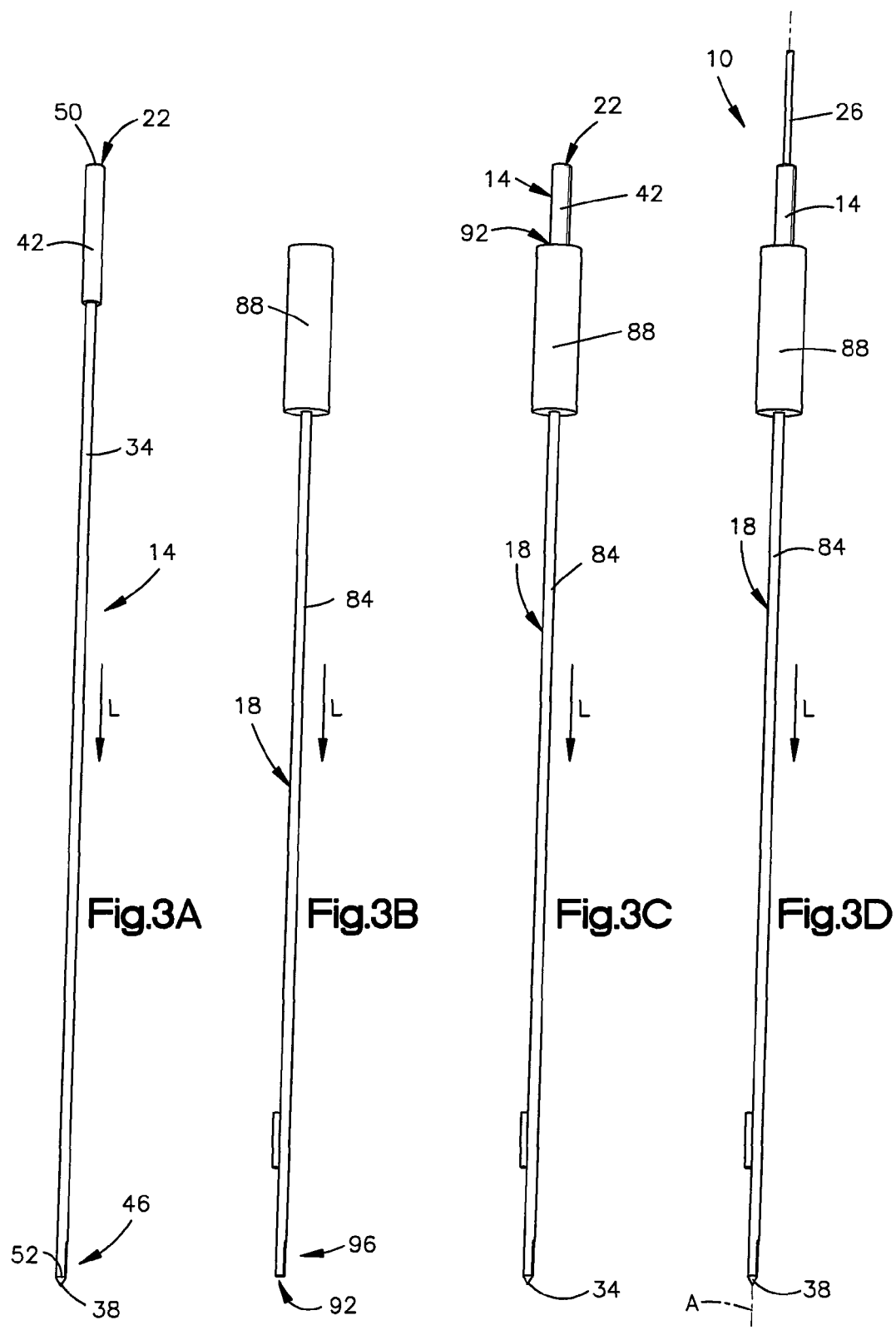

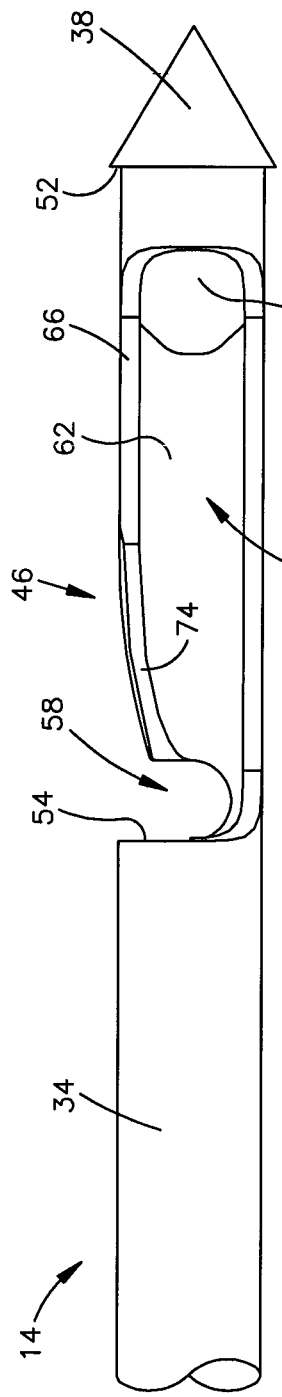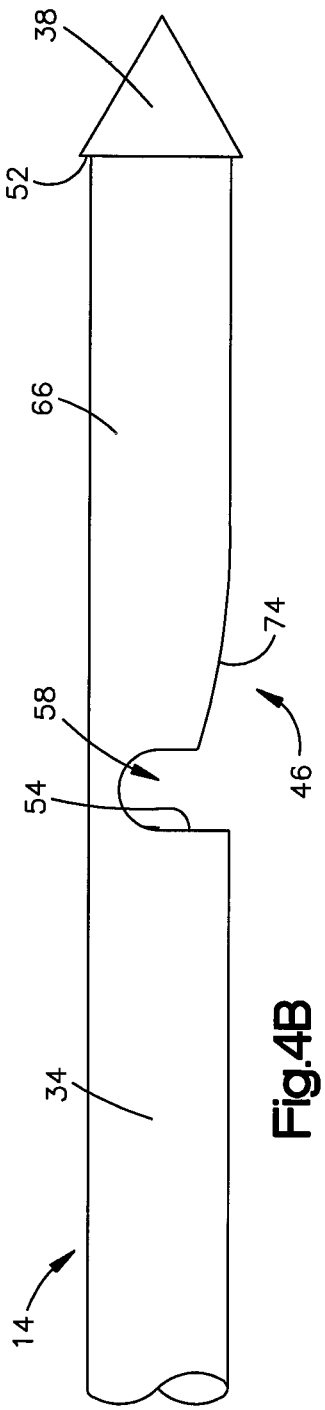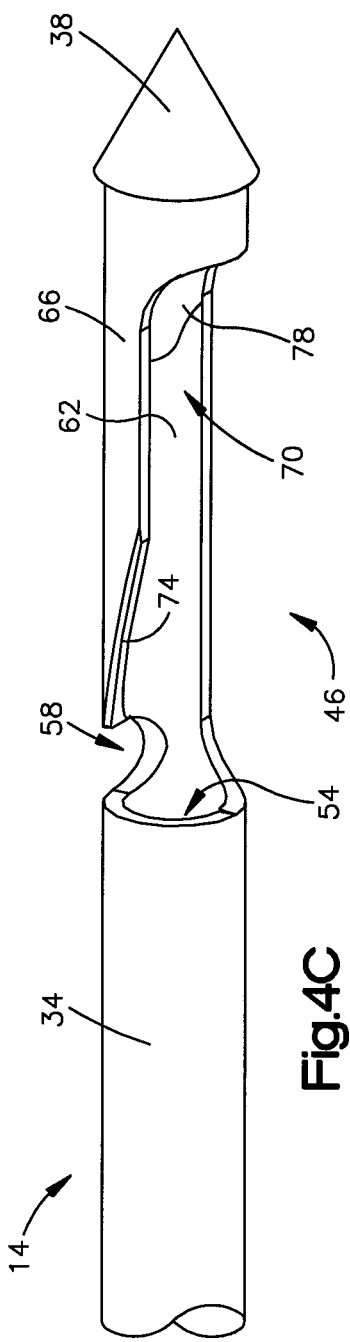

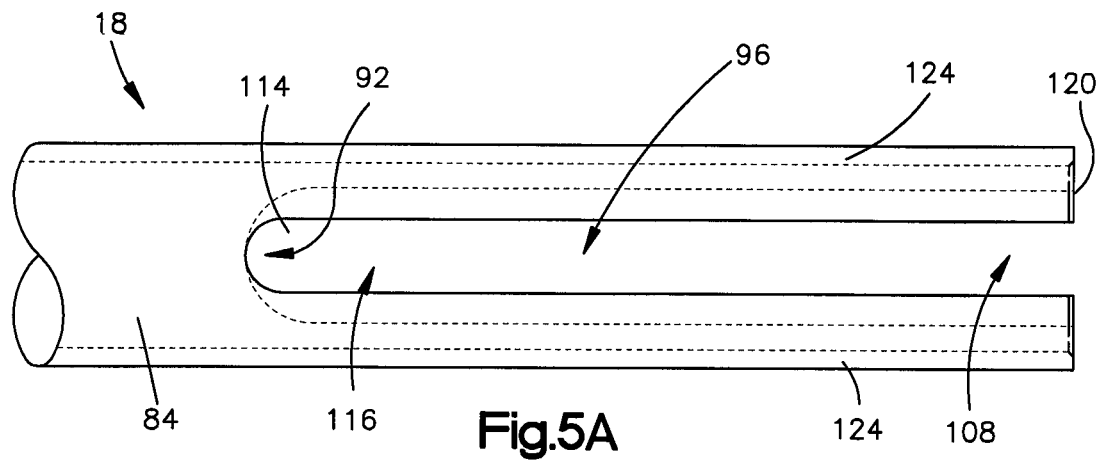
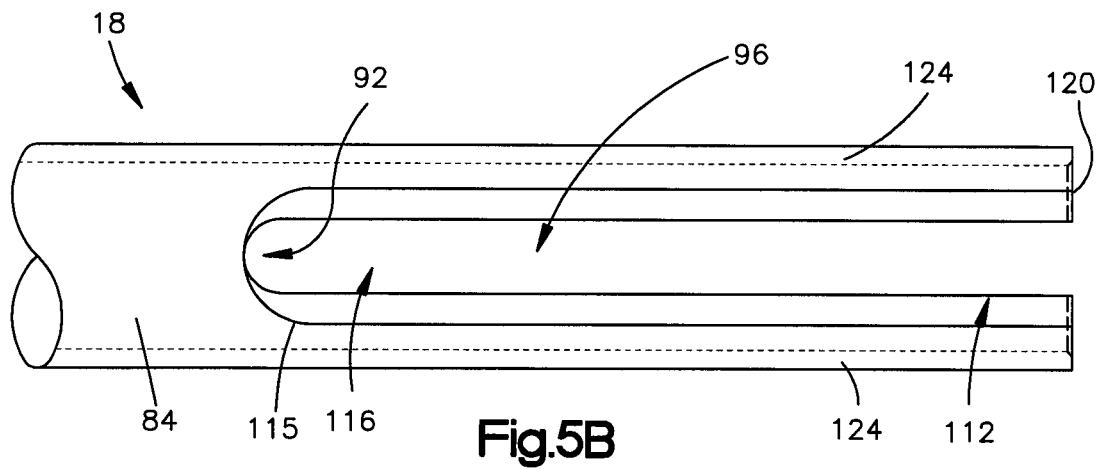
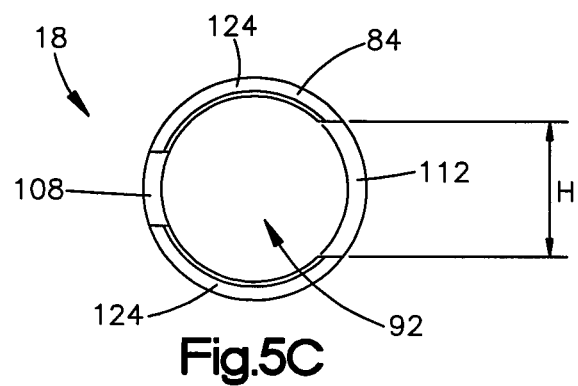

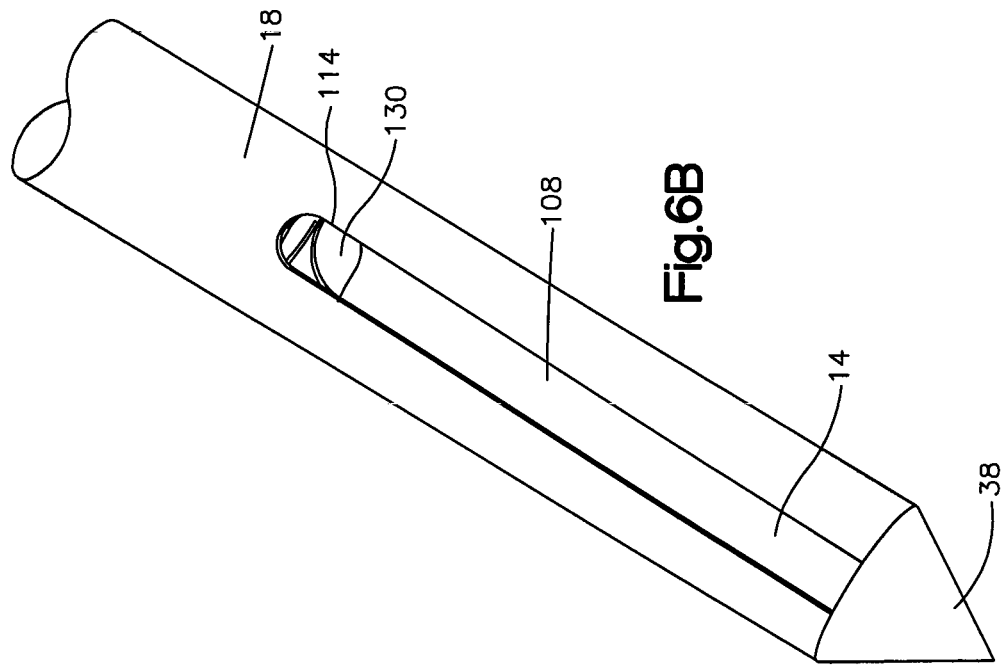
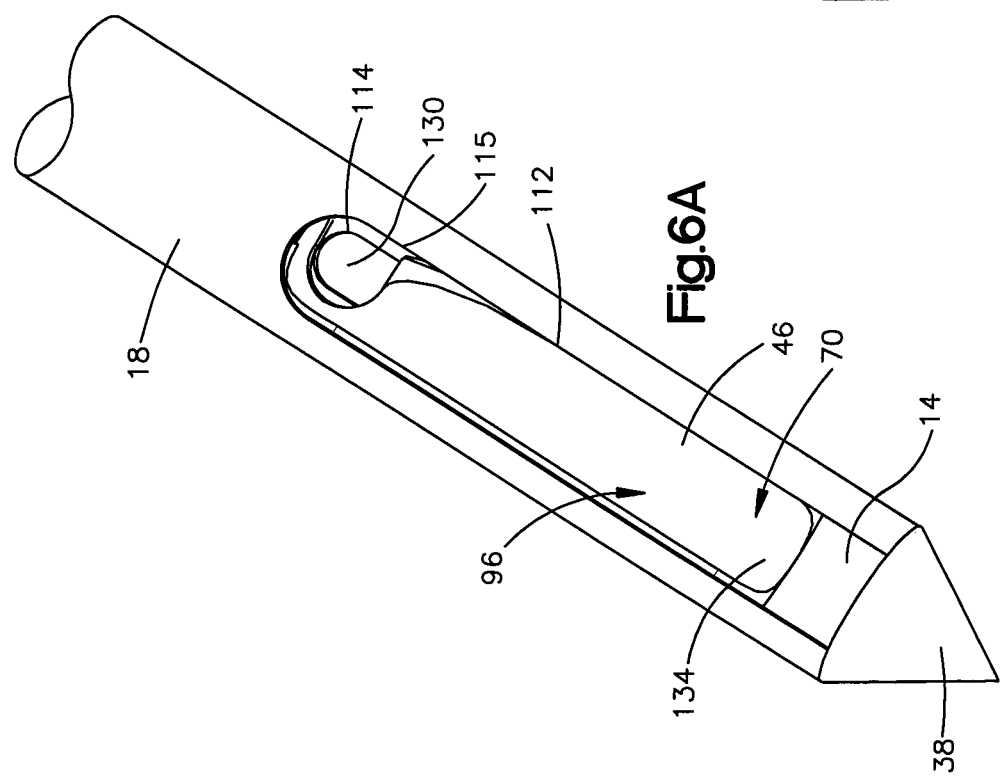

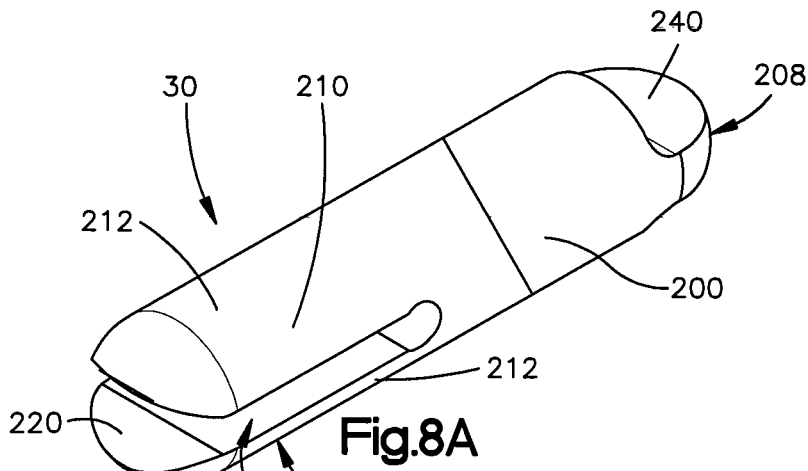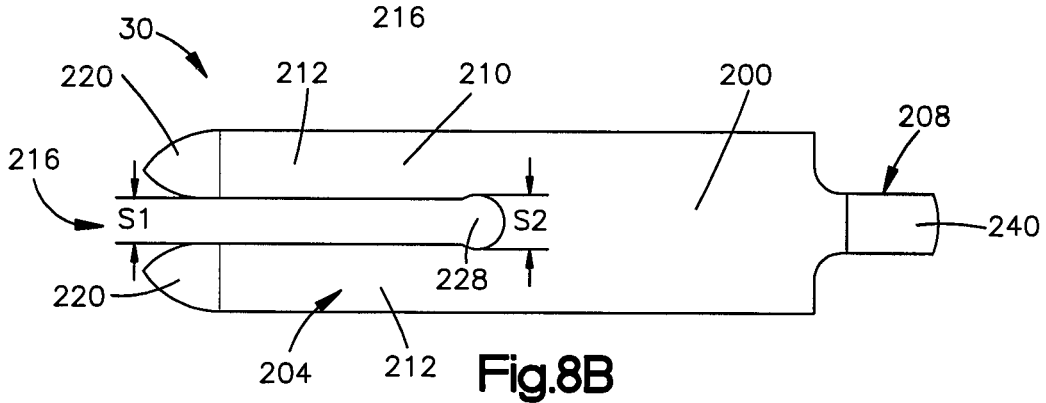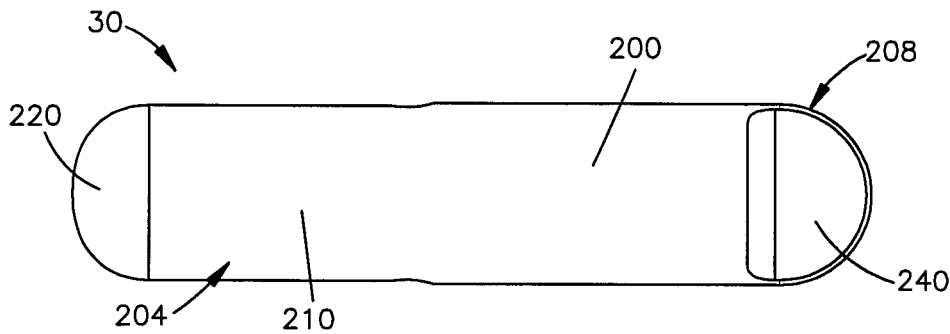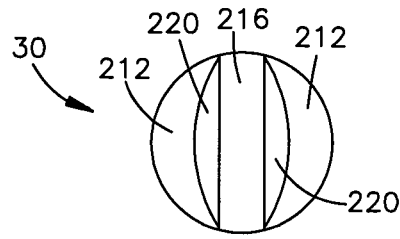

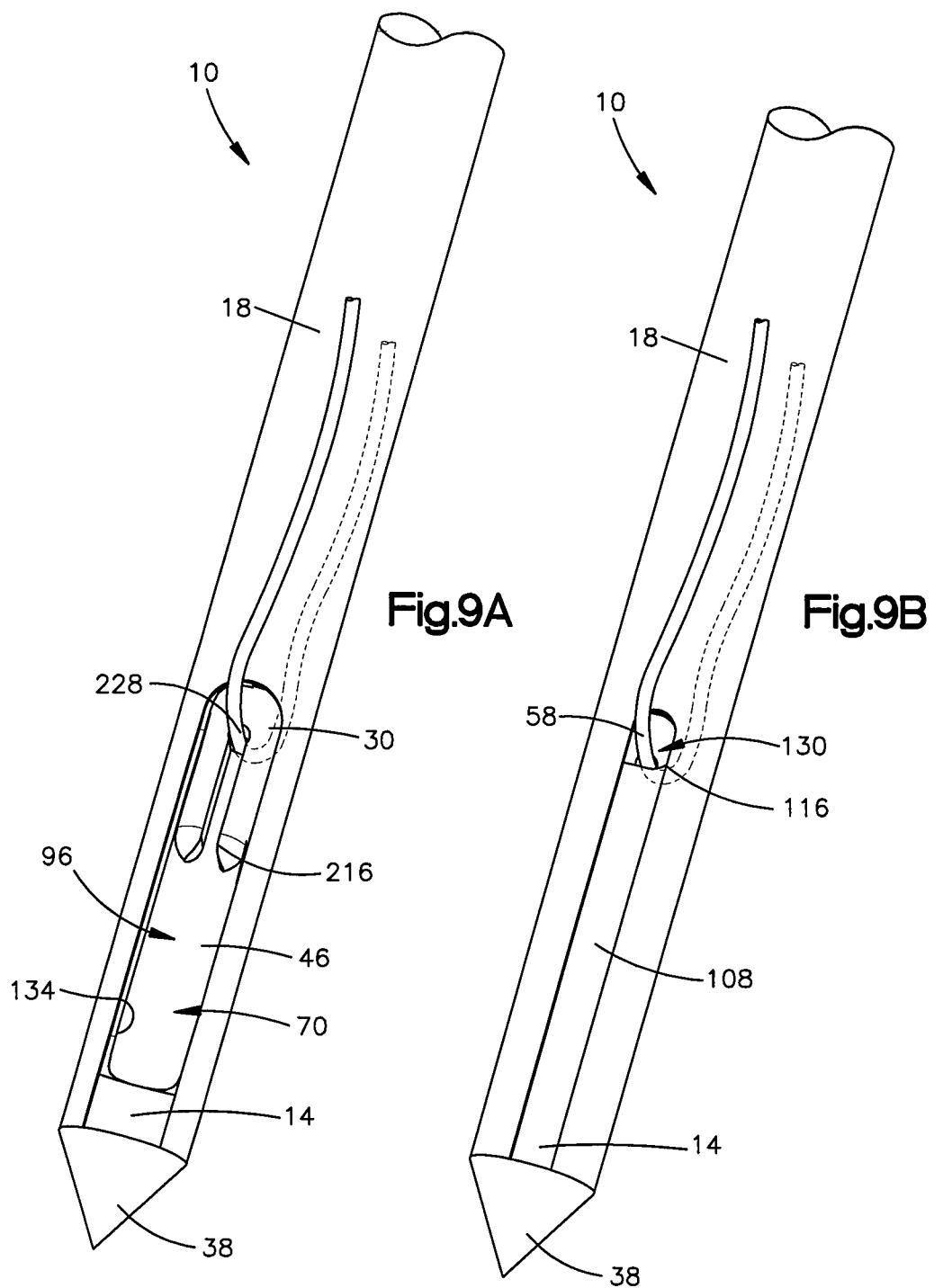

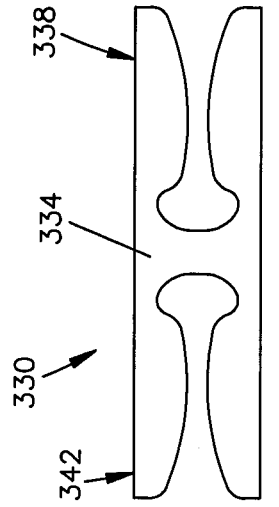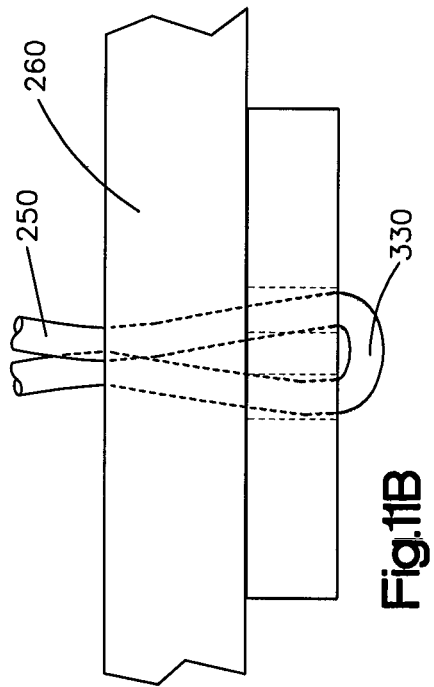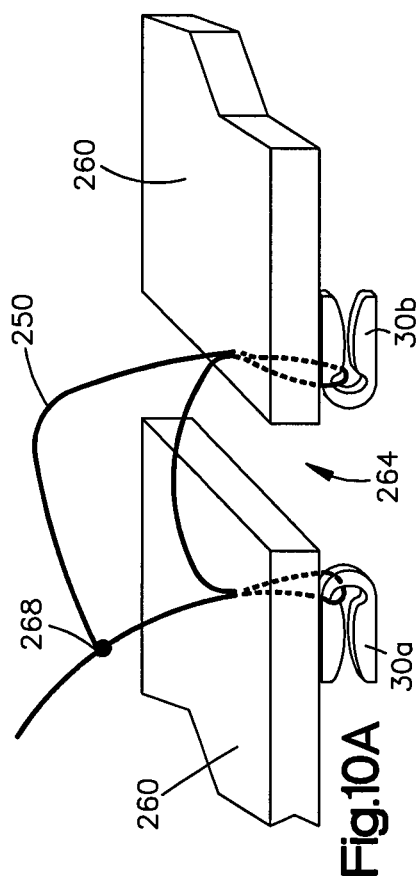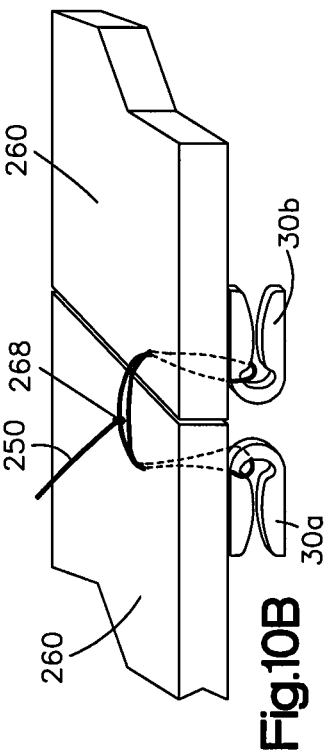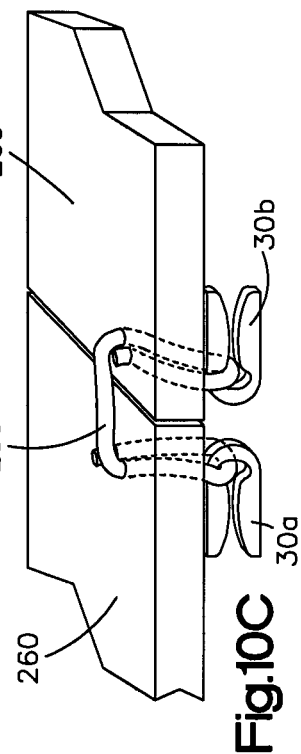

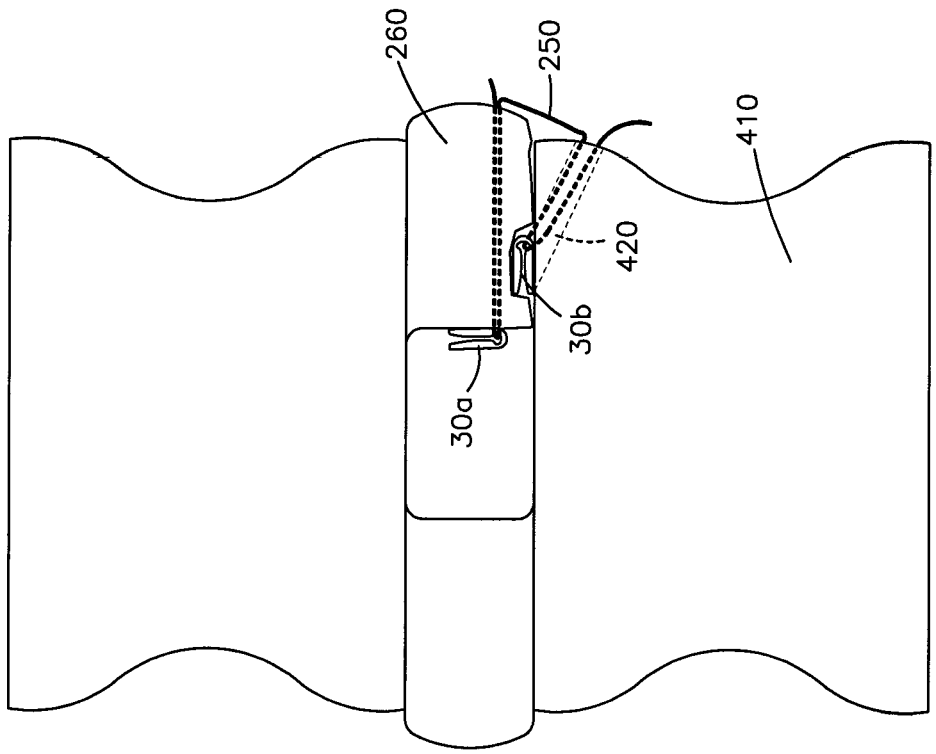
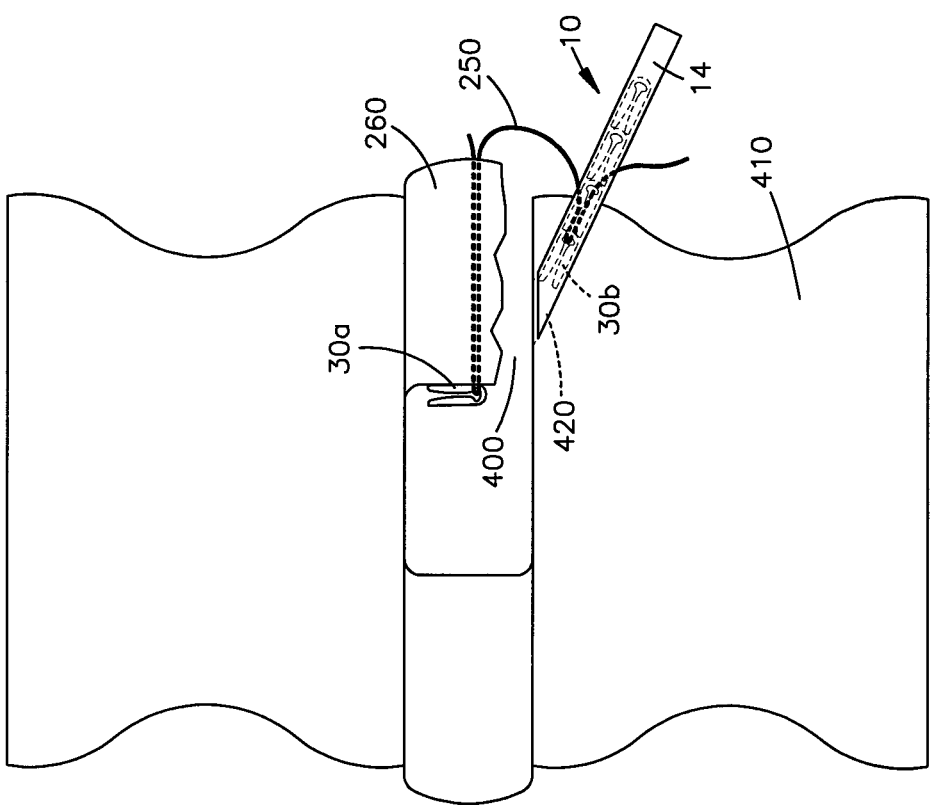

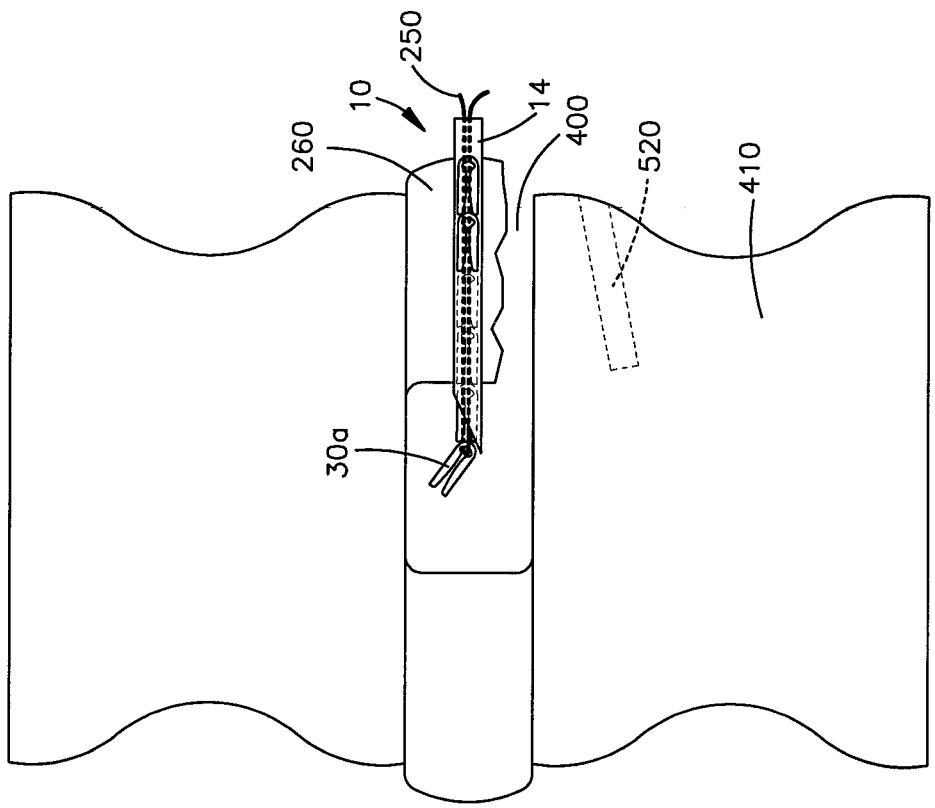
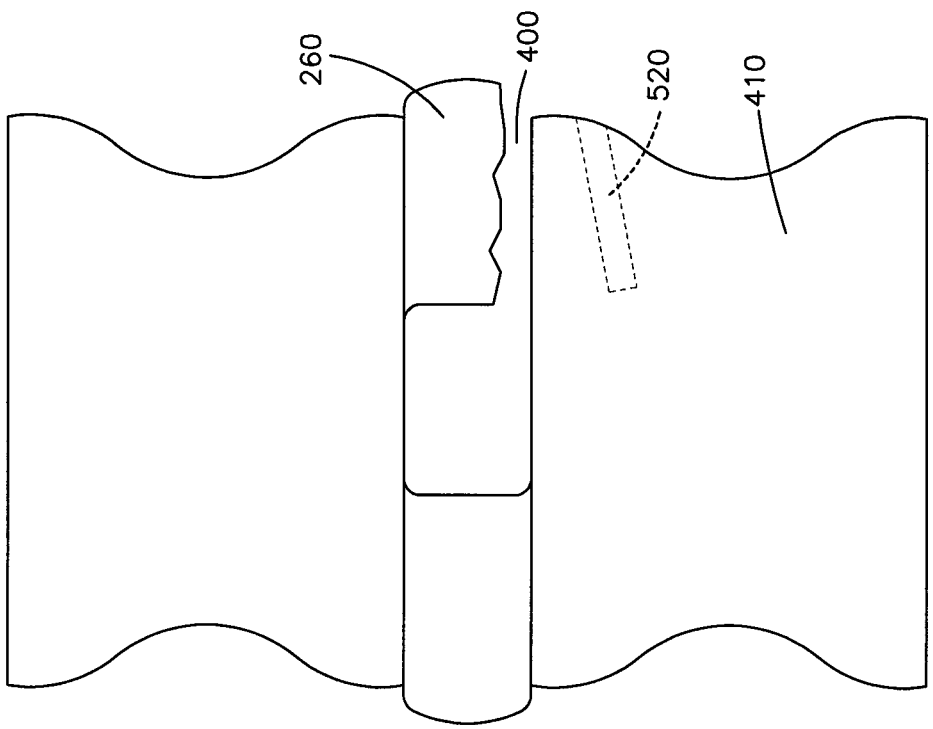

MULTI-STITCH ANCHOR SUTURE-BASED SOFT TISSUE REPAIR SYSTEM

CROSS REFERENCE TO RELATED APPLICATIONS

This application claims priority to U.S. provisional application 61/244,504 filed Sep. 22, 2009, the contents of which are incorporated by reference in their entirety.

BACKGROUND

A discectomy is a procedure that treats back pain, radiculopathy and/or myelopathy by surgically removing herniated nucleus pulposus to achieve neural decompression. Discectomy techniques involve removing intervertebral disc material through a hole in an annulus fibrosis of the disc, however such techniques typically do not repair the annular defect that is formed during the discectomy procedure. During the procedure, the surgeon may elect to remove only a herniated portion of nucleus impinging on the nerves, which treats the radiculopathy, but may increase the risk of post-operative reherniation of the remaining nucleus within the disc. Alternately, the surgeon may elect to perform extensive debulking, in which most of the remaining nucleus material is removed in addition to the herniated portion to minimize the risk of post-operative reherniation; however, the risk of post-operative disc height collapse and subsequent lower back pain may increase. Clinically patients tend to return to normal daily activities more quickly and suffer lessened disc degeneration when a limited discectomy is performed versus an extensive debulking of the disc. With current standard surgical practices, a hole or breach in an annulus is created, either pathologically due to a disc herniation, or by the surgeon during a nucleotomy or partial discectomy, and remains at the end of the procedure, leaving a pathway for future herniations.

SUMMARY

In one embodiment a soft tissue repair system may include a needle, a sheath, and an actuator. The needle may include a needle body and a tip extending from the needle body. The needle body may define an ejection port, and an elongate channel that is configured to house at least one suture anchor. The sheath may include a sheath body that is configured to be attached to the needle body and cooperate with the needle body so as to define a suture through hole disposed between the elongate channel and the ejection port. The suture through hole is configured to retain a strand of suture that extends transversely with respect to the elongate channel. The actuator may be configured to move in an ejection direction so as to push the suture anchor past the suture through hole to the ejection port, such that the suture anchor engages the suture strand as it passes the suture through hole, and is subsequently ejected from the needle out the ejection port.

In another embodiment a soft tissue repair system may be configured to retain a plurality of anchors and individually eject at least a first anchor of the plurality of anchors. The soft tissue repair system may include a needle and an actuator. The needle may include a needle body that is elongate in a longitudinal direction and a tip that extends from the needle body. The needle body may define a retention channel that extends along the longitudinal direction and is configured to retain a plurality of suture anchors. The needle body may further define an ejection port that is distal to the retention channel, and is configured to eject a first anchor of the plurality of anchors from the needle. A suture through hole may extend through the needle body along a direction transverse to the longitudinal direction between the retention channel and the ejection port. The suture through hole may be configured to retain a suture strand. The actuator may be configured to move the first anchor from the elongate channel, past the suture through hole, and to the ejection port, such that the first anchor can engage the suture strand as it passes the suture through hole and carry the suture strand as it is ejected from the ejection port.

Any one of the embodiments may be used for repairing soft tissue. For example, a device having a needle housed within a channel of a sheath may be provided. The needle may include a body and a tip that extends distally from the body. The needle body may define an elongate channel and an ejection port distal to the elongate channel. At least one suture anchor may be loaded into the needle channel. A strand of suture may be placed into the needle between the channel and ejection port such that the suture strand lies transverse to the needle body. The sheath may be advanced along the needle until a distal portion of the sheath holds the suture strand to the needle. The needle may then be advanced through a piece of tissue. Once through the tissue, the suture anchor may be pushed distally such that the suture anchor engages the strand of suture and is subsequently ejected from the ejection port.

BRIEF DESCRIPTION OF THE DRAWINGS

The foregoing summary, as well as the following detailed description of the preferred embodiments of the application, will be better understood when read in conjunction with the appended drawings. For the purposes of illustrating the soft tissue defect repair devices of the present application, there is shown in the drawings preferred embodiments. It should be understood, however, that the application is not limited to the precise arrangements and instrumentalities shown. In the drawings:

FIG. 1A is a perspective view of a soft tissue defect repair system in accordance with one embodiment, the system including a cannulated needle, and a sheath cooperating with the needle to hold a strand of suture to the needle, and an actuator pushing an anchor distally from within a channel of the needle to thereby capture the strand of suture with the anchor;

FIG. 1B is a perspective view of the soft tissue defect repair system of FIG. 1A with the actuator pushed further distally such that the anchor has been ejected from the needle;

FIG. 1C is a cross-sectional view of the soft tissue defect repair system of FIG. 1A, with all but one of the anchors ejected from the needle channel;

FIG. 3A is a top plan view of the cannulated needle of the soft tissue defect repair system shown in FIG. 1A;

FIG. 3B is a top plan view of the sheath of the soft tissue defect repair system shown in FIG. 1A.

FIG. 3C is a top plan view of the cannulated needle of FIG. 3A extending through a channel defined by the sheath of FIG. 3B;

FIG. 3D is a top plan view of an actuator extending through the channel of the cannulated needle shown in FIG. 3C;

FIG. 4A is a side elevation view of a distal portion of the cannulated needle shown in FIG. 3A;

FIG. 4B is a second side elevation view of the distal portion of the cannulated needle shown in FIG. 4A;

FIG. 4C is a third side elevation view of the distal portion of the cannulated needle shown in FIG. 4A;

FIG. 5A is a first side elevational view of a distal portion of the sheath shown in FIG. 3B;

FIG. 5B is a second side elevational view of the distal portion of the sheath shown in FIG. 5A;

FIG. 5C is a front plan view of the distal portion of the sheath shown in FIG. 5A;

FIG. 6A is a first side elevational view of the distal portion of the soft tissue defect repair system, when the sheath is in an ejection (first) position;

FIG. 6B is a second side elevational view of the distal portion of the soft tissue defect repair system shown in FIG. 6A;

FIG. 8A is a top perspective view of a suture anchor to be inserted into the needle channel of the soft tissue defect repair system shown in FIG. 1A;

FIG. 8B is a side elevational view of the suture anchor shown in FIG. 8A;

FIG. 8C is a top plan view of the suture anchor shown in FIG. 8A;

FIG. 8D is a front elevational view of the suture anchor shown in FIG. 8A;

FIG. 9A is a top plan view of the distal portion of the soft tissue defect repair system shown in FIG. 6A further including the suture anchor shown in FIG. 8A and a strand of suture;

FIG. 9B is a bottom plan view of the distal portion of the soft tissue defect shown in FIG. 9A;

FIG. 10A is a perspective view of soft tissue separated by a defect;

FIG. 10B is a perspective view of the soft tissue of FIG. 10A approximated by the soft tissue defect repair system of FIG. 1A;

FIG. 10C is a perspective view of the soft tissue of FIG. 10A approximated by the soft tissue defect repair system of FIG. 1A using an anchor that captures but does not lock the suture;

FIG. 11A is a side elevational view of a suture anchor in accordance with another embodiment;

FIG. 11B is a perspective view of soft tissue that has been approximated by the soft tissue defect repair system of FIG. 1A using the suture anchor of FIG. 11A;

FIG. 13C is a side view of the soft tissue defect repair system of FIG. 13B being advanced through a transosseous tunnel of the bony element, and ejecting a second suture anchor;

FIG. 13D is a side view of the soft tissue defect after it has been approximated;

FIG. 14A is a side view of a soft tissue defect adjacent to a bony element defining a transosseous tunnel that terminates within the bony element;

FIG. 14B is a side view of the soft tissue defect repair system of FIG. 1A being advanced through soft tissue and ejecting a first suture anchor;

DETAILED DESCRIPTION OF ILLUSTRATIVE EMBODIMENTS

Figure 2:
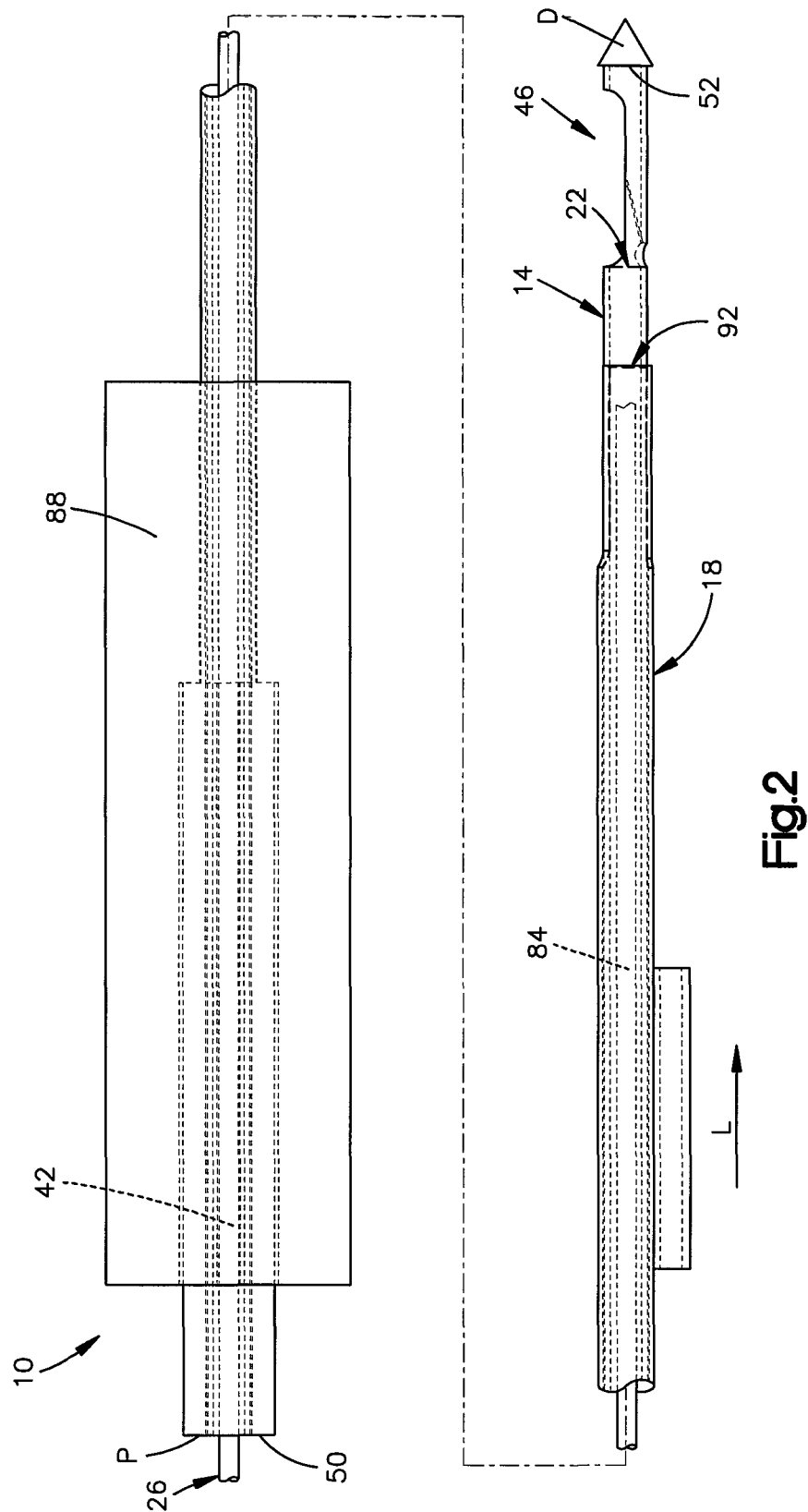
FIG. 2 is a top plan view of the soft tissue defect repair system of FIG. 1A with no anchors disposed within the needle channel.

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the geometric center of the preferred soft tissue defect repair systems and related parts thereof. The words, "anterior", "posterior", "superior," "inferior", "medial", "lateral" and related words and/or phrases designate preferred positions and orientations in the human body to which reference is made and are not meant to be limiting. The terminology includes the above-listed words, derivatives thereof and words of similar import.

In reference to FIGS. 1A-1C, a soft tissue defect repair system 10 constructed in accordance with one embodiment is configured to approximate a soft tissue, such as the annulus fibrosis of an intervertebral disc, having a defect, such as a fissure. The system 10 utilizes a plurality of anchors that are individually placed to repair the tissue. As shown, the soft tissue defect repair system 10 is elongate in a longitudinal direction L, and includes a proximal end P and a distal end D. The soft tissue defect repair system 10 includes a cannulated needle 14, and a sheath 18 disposed about and translatable with respect to the cannulated needle 14. When the sheath 18 has been translated to a first position as shown in FIGS. 1A and 1B, the needle 14 and the sheath 18 cooperate with each other to releasably hold a strand of suture 20 to the needle 14 such that the suture strand intersects a longitudinally elongate channel 22 of the needle 14. As best shown in FIG. 1C, the soft tissue defect repair system 10 further includes a translatable actuator 26 disposed in the channel 22 of the cannulated needle 14. The actuator 26 is configured to push a plurality of suture anchors, such as suture anchors 30 shown in FIGS. 8A-8D, that are stacked one after another within the channel 22 of the cannulated needle 14 and distal to the actuator 26. The suture anchors 30 may be individually loaded into the needle channel 22 and used as they are individually loaded, or they may all be pre-loaded into the needle channel 22 at one time and then used. Once anchors 30 have been loaded into the channel 22 and the suture strand has been properly placed, the actuator 26 may be advanced distally to push the anchors 30 or at least a first anchor 30 distally until it captures the strand of suture that is held to the needle as shown in FIG. 1A. Further advancement of the actuator 26 will cause the first anchor 30 to be displaced or otherwise ejected from the needle 14 as shown in FIG. 1B.

As shown in FIGS. 1A-1C, 2, and 3A, the cannulated needle 14 includes a body 34 that is elongate in the longitudinal direction L and extends along a central longitudinal axis, a tip 38 that extends distally from the body 34, and a handle 42 that extends proximally from the body 34. The handle 42 may be trapped or otherwise contained within the handle 88. As shown, the handle 42 is oblong and has a diameter that is greater than the diameter of the needle body 34. While the handle 42 is shown as being oblong, it should be understood that the handle 42 may include other shapes and designs, for example the handle may be cylindrical.

The needle 14 further includes a channel 22 that extends through the needle body 34 in the longitudinal direction L and opens up to an anchor ejection port 46 that is disposed proximal to the needle tip 38. The channel 22 can be cylindrical, or alternatively shaped, and is configured to house a plurality of suture anchors 30. In this way, channel 22 may be considered a retention channel. The suture anchors 30 may be loaded into the channel 22 along a longitudinal loading direction through a proximal opening 50 of the channel 22. In this regard, a first suture anchor 30 may be loaded into the channel 22 through the proximal opening 50, and once loaded, a second suture anchor 30 may be loaded into the channel 22 through the proximal opening 50, and so on. In this way, the suture anchors 30 are considered to be stacked one after another.

As shown in FIGS. 1A-1C, and 4A-4C, the needle tip 38 extends distally from the needle body 34 and is configured to penetrate a piece of tissue. As shown, the needle tip 38 is generally conical distally tapered and includes a shoulder 52 at its proximal end that has a diameter that is greater than the diameter of the needle body 34. The shoulder 52 may have a diameter that is equal to the diameter of the sheath 18. While the needle tip 38 is conical, it should be understood that the needle tip 38 may have any shape so long as it is capable of penetrating tissue or bone. For example the needle tip 112 may be an awl tip and could be used to create a transosseous bone tunnel.

As best shown in FIGS. 4A-4C, the channel 22 extends through the body 34 and into the ejection port 46 of the needle body 34. In particular, the channel 22 includes a distal opening 54 that transitions the channel 22 to the ejection port 46. As best shown in FIG. 4A, the ejection port 46 is a distal portion of the needle body 34 that is cut away or otherwise open so as to expose the channel 22 to the external environment and allow a suture anchor 30 to be displaced or otherwise ejected from the needle 14. As shown, between the channel opening 54 and the ejection port 46 is a transverse opening 58 that extends transversely through the needle body 34 proximate to the distal opening 54 of the channel 22. The transverse opening 58 is defined by a surface 60 and is configured to receive and hold a strand of suture such that the strand of suture extends transversely across or otherwise intersects the needle body 34. It should be understood that transverse means that the opening and the suture strand extend across the needle body 34 at some angle with respect to the longitudinal direction L. Preferably, however, the opening and suture strand lie perpendicular to the longitudinal direction L.

As shown in FIGS. 4A-4C, as the ejection port 46 extends distally from the transverse opening 58, the ejection port 46 defines a substantially U-shaped channel 62, which may be considered an extension of the needle channel 22. As shown, the U-shaped channel 62 is defined by a channel wall 66 having a top opening 70 that exposes the channel 62 to the external environment. The top opening 66 is wide enough to allow the suture anchors 30 to be displaced from the needle 14 as the suture anchors 30 are pushed distally. The channel wall 66 further includes an angled portion 74 that angles up as the wall 66 extends distally from the transverse opening 58. The angled portion 74 allows the strand of suture to be more easily released or disengaged from the transverse opening 58 when it is desired to release the strand of suture. As best shown in FIG. 4A, a distal portion of the U-shaped channel 62 defines a ramp 78 that is configured to direct the suture anchors 30 through the top opening 70 and out of the channel 62 as the suture anchors 30 are pushed distally.

As shown in FIGS. 1A-1C, 2, and 3C-3D, the system 10 includes a sheath 18 that is disposed coaxially around the exterior of the needle 14 and is translatable with respect to the needle 14 along the longitudinal direction L. As shown, the sheath 18 includes a body 84 that is elongate in the longitudinal direction L, and a handle 88 that extends proximally from the body 34. The sheath 18 further includes a channel 92 that extends through the sheath body 34 in the longitudinal direction L and opens up to a sheath ejection port 96 that is defined by a distal portion of the sheath body 84. The channel 92 is cylindrical and is configured to receive the needle 14. The channel 92 has a diameter that allows the sheath 18 to translate relative to the needle body 34. That is, either the needle 14 or the sheath 18 is translated along a portion of the other so that one moves relative to the other. In the illustrated embodiment the sheath 18 is configured to translate along the needle body 34 between a distal first position and a proximal second position.

As shown in FIGS. 1A, and 3B-3D, the sheath handle 88 extends proximally from the sheath body 84 and is configured to be held by a user. As shown, the handle 88 is cylindrical and defines a cavity configured to house the needle handle 42. As shown in FIG. 1A, the cavity is oblong and is configured to hold the oblong handle 42 of the needle 14. The shaped cavity prevents the needle from falling out of the sheath 18. While the handle 88 is shown as being cylindrical, it should be understood that the handle 88 may include other shapes and designs so long as it can be grabbed and held by the user.

As best shown in FIGS. 5A-5C, the sheath channel 92 extends into and through the ejection port 96. As best shown in FIG. 5A, the sheath ejection port 96 is defined by a distal portion of the sheath body 84 that is open or otherwise cut away so as to expose the channel 92 to the external environment and allow a suture anchor 30 to be displaced from the needle 14 and sheath 18. As shown, the ejection port 96 is defined by two opposing slots 108, 112 that extend transversely through the sheath body 84 and include surfaces 114 and 115 respectively. The slots 108 and 112 are aligned and define a transverse opening 116 that is configured to receive and hold the strand of suture that is held by the transverse opening 58 of the needle body 34. As shown, the opening 116 extends along the entire longitudinal length of the slots 108, 112 and is accessible through a distal end 120 of the sheath body 84. In this regard, it can also be said that the sheath ejection port 96 is defined by two opposing cantilevered semi-circular beams 124 that are separated by the transverse opening 116. Therefore the ejection port 96 of the sheath 18 is designed such that as the sheath 18 is translated distally with respect to the needle 14, the strand of suture that is held in the transverse opening 58 of the needle body 34 will enter the sheath transverse opening 116 through the distal end 120 of the sheath body 84. When the sheath 18 is fully translated to its distal first position, the transverse openings 58 and 116 of the needle 14 and the sheath 18 align (as shown in FIGS. 6A, and 6B) to thereby form a suture through hole 130 that is configured to hold or otherwise attach the strand of suture to the needle and thus the soft tissue defect repair system 10. In particular, the surfaces 114, 115, and 60 of the needle 14 and the sheath 18 define the through hole 130. When the sheath 18 is translated proximally, the surfaces 114 and 115 of the sheath no longer define part of the through hole 130, thereby providing an opening through which the suture strand may be removed from the needle 14. It should be understood that in some embodiments the needle itself defines the suture through hole 130.

Now referring to FIG. 5C, the slot 112 has a greater height than the slot 108. As shown, the slot 112 has a height H that is configured to allow the suture anchor 30 to pass therethrough. As shown in FIG. 6A, when the sheath 18 is fully translated to its first position the slot 112 of the sheath 118 is aligned with the top opening 70 of the needle ejection port 46 to thereby form a dispensing slot 134 for the suture anchor 30 to exit as the suture anchor 30 is pushed distally. While the slot 112 is shown as having a greater height than slot 108, it should be understood that the slots 108, and 112 may have any height so long as one of the slots 108, 112 has a height that is great enough to allow the suture anchor 30 to pass therethrough.

Figure 7A:
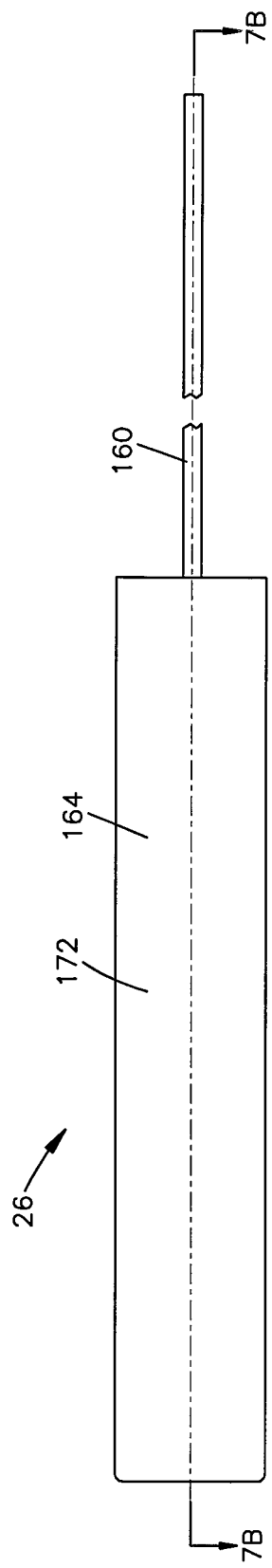
FIG. 7A is a top plan view of the actuator of the soft tissue defect repair system shown in FIG. 1A.
Figure 7B:
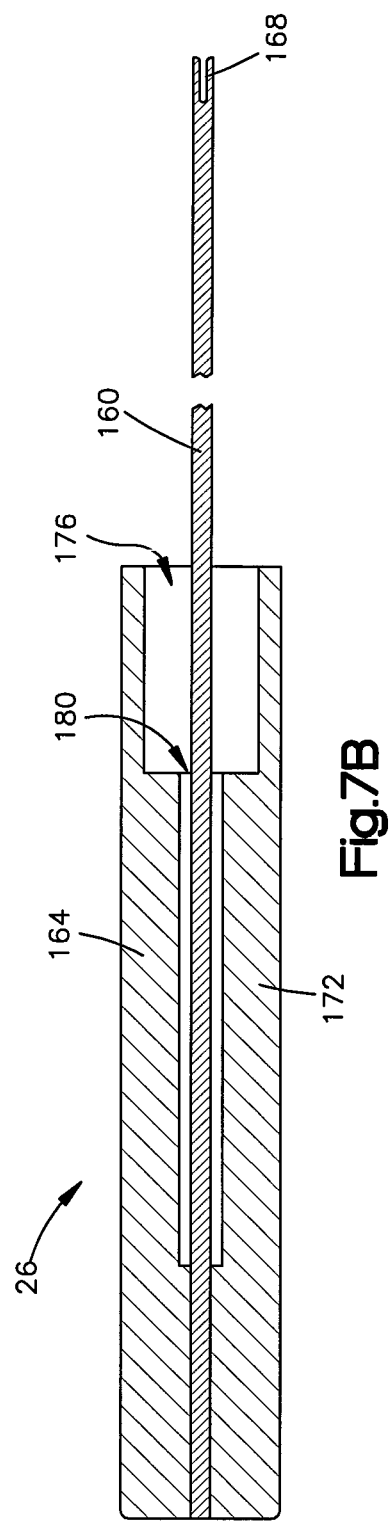
FIG. 7B is a cross-sectional view of the push rod shown in FIG. 7A through the line 7B-7B.

As shown in FIGS. 1A, 3D, 7A, and 7B, the system 10 includes an actuator 26 that is configured to translate within the channel 22 of the needle 14 and push the suture anchors 30 distally. In the illustrated embodiment, the actuator 26 is a push rod. As shown in FIGS. 7A and 7B, the actuator 26 includes a shaft 160 that is elongate in the longitudinal direction L, and a handle 164 that is coupled to a proximal end of the shaft 160. Generally, the shaft 160 is cylindrical and has a diameter that allows it to translate within the channel 22 of the needle 14. As shown in FIG. 7B, a distal end of the shaft 160 includes an engagement feature such as a groove 168 that is configured to engage and mate with the proximal end of a suture anchor 30.

As shown in FIG. 7B, the handle 164 of the actuator 26 includes a body 172 that is elongate in the longitudinal direction L. The body 172 defines a first bore 176 that extends proximally from a distal end of the body 172. The body 172 further defines a second bore 180 that extends proximally from a proximal end of the first bore 176. The first bore 176 has a first diameter and is configured to receive the handle 42 of the needle 14 when the actuator 26 is advanced distally.

As shown in FIGS. 8A-8D, the soft tissue defect repair system 10 may include a plurality of suture anchors 30 that are stacked one after the other within the channel 22 of the needle 14. As shown, each suture anchor 30 includes a body 200 that is elongate in the longitudinal direction L. The distal end of the body 200 defines a suture engagement feature 204 configured to engage the suture strand, and the proximal end of the body 200 defines a push rod engagement feature 208 that is configured to be engaged by the distal end of the actuator 26. If multiple suture anchors 30 are loaded into the needle 14, the suture engagement feature 204 of a second suture anchor 30b will engage the push rod engagement feature 208 of a distal first suture anchor 30a. As can be appreciated by those skilled in the art, the suture anchors 30 may be made of a bio-compatible material, such as, stainless steel, titanium, PEEK, nitinol, PET, or any other at least semi-rigid material known in the art.

As shown in FIGS. 8A-8D, the suture engagement feature 204 may be a locking cleat 210 having two opposing distally extending members 212 that are separated by a transverse slot 216 that is configured to receive the strand of suture that is locked in the through hole 130 defined by the needle 14 and sheath 18. As shown in FIG. 8B, a distal end 220 of each member 212 is tapered so as to guide the suture strand into the slot 216 as the suture anchor 30 is advanced distally through the needle channel 22. The slot 216 extends proximally into the anchor body 200 and terminates at a transverse generally cylindrical groove 228. The slot 216 generally has a first height S1, and the groove 228 generally has a second height (or diameter) of S2 that is greater than the first height S1. The first height S1 is also smaller than the diameter of the strand of suture. Therefore, as the slot 216 receives the strand of suture, the members 212 flex outwardly or otherwise away from each other so as to allow the strand of suture to travel down the slot 216 and into the groove 228. Once the strand of suture is received within the groove 228, the members 212 return to their normal position and lock the strand of suture within the groove 228 and thus to the suture anchor 30. Generally, the diameter S2 of the groove 228 is equal to or slightly less than the diameter of the suture stand so that the suture strand does not move within the groove 228. It should be understood however, that the groove 228 may be sized to capture the suture strand and not lock the suture strand to the anchor 30 so as to allow the suture strand to move within the groove 228. Any combination of anchors 30 with capturing and/or locking features may be utilized.

As shown in FIGS. 8B and 8C, the push rod engagement feature 208 of the anchor 30 may be a proximally extending tongue 240. As shown in FIG. 8C, the tongue 240 is parallel to the slot 216 so that the stacked suture anchors 30 engage each other as they are pushed distally within the needle channel 22 and act as an extension of the push rod as they are pushed distally. As shown in FIG. 8B, a proximal end of the tongue 240 is curved and is configured to be received within the groove 168 that is defined by the distal end of the push rod shaft 160. Therefore, when the tongue 240 of the suture anchor 30 is engaged by the groove 168 of the actuator 26, the slot 216 of the suture anchor 30 will be properly aligned to engage the suture strand that is retained in the through hole 130 defined by the needle 14 and sheath 18.

In operation and in reference to FIGS. 9A, 9B, 10A and 10B, a strand of suture 250 is loaded into and releasably retained by the soft tissue defect repair system 10 by placing the suture 250 within the transverse opening 58 defined by the needle body 34 between the retention channel 22 and the ejection port 46. Once placed, the sheath 18 may be advanced distally to its first position as shown in FIG. 9B such that the transverse opening 116 of the sheath 18 is aligned with the transverse opening 58 of the needle 14. The aligned openings 58, 116 create a suture through hole 130 that captures and retains the suture strand 250, such that the strand of suture 250 extends through the needle 14 and sheath 18 transversely with respect to the longitudinal axis of the soft tissue defect repair system 10. The free ends of the suture 250 may be held in tension and releasably retained by a cleat (not shown) or may be tied together with a sliding knot to form a suture loop. A first suture anchor 30a is loaded into the proximal opening 50 of the needle channel 22 such that the slot 116 formed by the locking cleat 112 is facing the distal end of the system 10. In a preferred embodiment, a plurality of anchors 30a-30n are pre-loaded axially or otherwise stacked within the channel 22 of the needle 14. The suture strand that is held in tension prevents the anchors 30 from inadvertently falling out of the needle 14.

The soft tissue defect repair system 10 is then grasped and the needle tip 38 is advanced through the full thickness of a soft tissue 260 (e.g., through the entirety of the annulus fibrosis and into the nucleus space) from a first (outer) side to second (inner) side of the tissue 260 adjacent a defect 264 in need of repair, such as a fissure through the annulus fibrosis of an intervertebral disc. The push rod handle 164 is grasped and displaced by an operator such that the actuator 26 is translated distally with respect to the needle 14, thereby engaging the proximal end or tongue 240 of the anchor 30 and translating the anchor 30 distally. As the anchor 30 is translated distally the suture 250 is received into the slot 216 of the anchor 30 and is eventually captured within the groove 228 of the anchor 30 to thereby capture and lock the suture 250 to the anchor 30. As the actuator 26 is further translated, the anchor 30 and thus the suture 250 is displaced or translated distally with respect to the needle 14, as shown in FIG. 9A. It should be understood, that the actuator 26 may instead be permanently coupled to the needle 14 and actuated by a mechanism such as a trigger or button (not shown).

As the actuator 26 continues to translate distally with respect to the needle 14, the anchor 30 is ejected from the dispensing slot 134 defined by the aligned slot 112 of the sheath 18 and the opening 70 defined by the needle ejection port 46. The anchor 30 is at this point passed to the second side of the tissue 260, thereby locking the suture 250 into place interior to the second side of the tissue 260 (e.g., on the interior wall of the annulus fibrosis). The actuator 26 is then retracted and the needle tip 38 passes back through the tissue to the first side of the tissue 260 pulling the suture strand with it through the same initial hole.

At this point the soft tissue defect repair system 10 is still loaded with the suture 250 and the needle tip 38 is moved to a different point adjacent the defect 264, such as on the opposite side of the defect 264 as shown in FIGS. 10A and 10B. The soft tissue defect repair system 10 is again grasped and the needle tip 38 is advanced through the full thickness of the soft tissue 260 from a first (outer) side to second (inner) side of the tissue adjacent the defect 264 in need of repair. Tension is then applied to the suture strand 250 to partially reapproximate the soft tissue defect 264 as shown in FIG. 10B. Once the tissue 260 is reapproximated the method steps may be repeated with a second anchor 30b. These steps can be repeated as many times as is desired to implant the desired number of anchors 30a-n on the second side of the tissue 260 adjacent the defect 264. In embodiments where the anchor includes a capturing cleat, both the first and second anchors are ejected and then the tissue is approximated as shown in FIGS. 10A and 10B. In embodiments where the anchor includes a locking cleat, the tissue is approximated prior to the second anchor being ejected as shown in FIG. 10C.

At the end of the procedure, the sheath 18 is retracted to its second position by grasping and displacing proximally the sheath handle 88 to thereby release the suture 250 from the needle 14. In embodiments where the anchor includes a locking cleat, the suture 250 is then cut adjacent the surface of the first side of the tissue 260. The suture ends could instead be secured by tying a knot against the first side of the tissue.

In embodiments where the anchor 30 only captures the suture as shown in FIGS. 10A and 10B, the suture can be cinched into final tightening with the pre-tied sliding knot 268 to reapproximate the tissue, with the knot 268 coming to rest on the first side of the tissue (e.g., exterior to the annulus fibrosis) near the insertion point of the first anchor 30a, as is shown in FIG. 10B. A simple knot pusher device, as is known in the art, can be utilized to slide the knot 268 toward the surface of the tissue during the cinching step. The suture ends could instead be secured by tying a knot against the first side of the tissue.

In an alternative embodiment and in reference to FIGS. 11A and 11B, the anchor may include distal and proximal suture engagement features. As shown in FIG. 11A, an anchor 330 includes a body 334 that is elongate in the longitudinal direction L. The distal end of the body 334 defines a suture engagement feature 338 configured to engage the suture strand, and the proximal end of the body 334 defines a suture engagement feature 342 that is also configured to engage the suture strand. The suture engagement features 338 and 342 may be constructed to be similar to the suture engagement feature 204 of the anchor 30 shown in FIGS. 8A-8D. By having opposing suture engagement features 338 and 342 there may be two locking points of contact at each insertion point as shown in FIG. 11B.

Figure 12A:
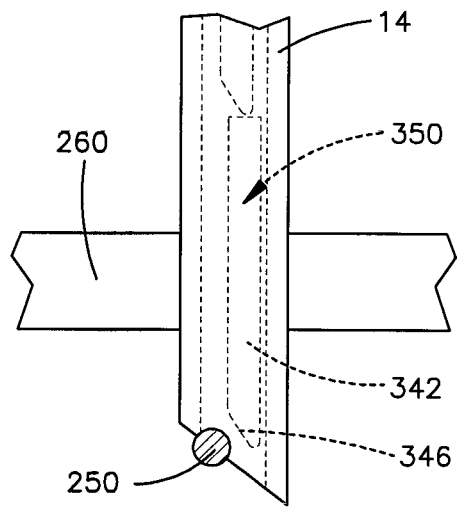
FIG. 12A is a side view of a soft tissue defect repair system in accordance with another embodiment and approximating soft tissue.
Figure 12B:
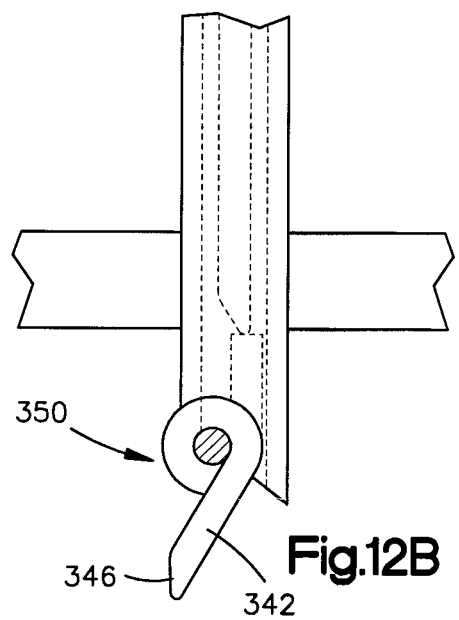
FIG. 12B is a side view of a first suture anchor being discharged from the soft tissue defect repair system of FIG. 12A.
Figure 12C:
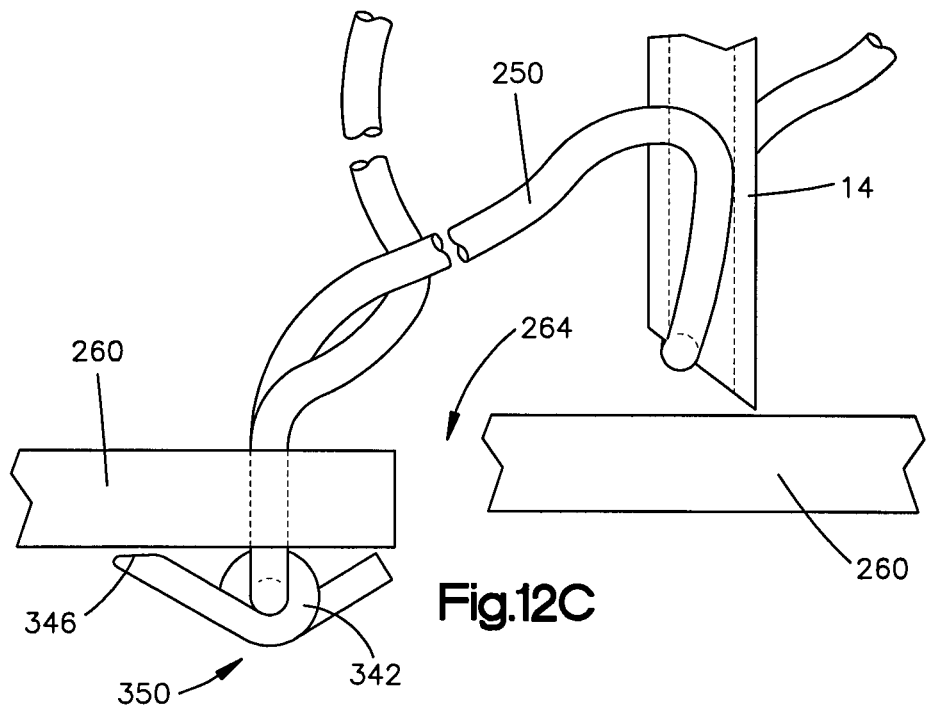
FIG. 12C is a side view of the soft tissue defect repair system of FIG. 12B being inserted into the tissue on an opposite side of the defect.

In an alternative embodiment and in reference to FIGS. 12A-12C, the anchor may be a wire coil formed of a shape memory material such as nitinol. As shown in FIGS. 12A and 11B, an anchor 350 may be a wire coil 342 having a tapered distal end 346. The wire coil 342 is straight once it is loaded within the channel 22 of the needle 14. Upon deployment of the anchor 350, the wire coil 342 begins to assume a pre-shaped helical configuration while simultaneously engaging and capturing the suture 250 that is retained proximate to a distal end of the needle 14. As shown in FIG. 12C, the fully dispensed wire coil 342 is fixed to the suture 250 on the inside of the tissue 260 and the tapered end 346 abuts the inside surface of the tissue 260.

Figure 13B:
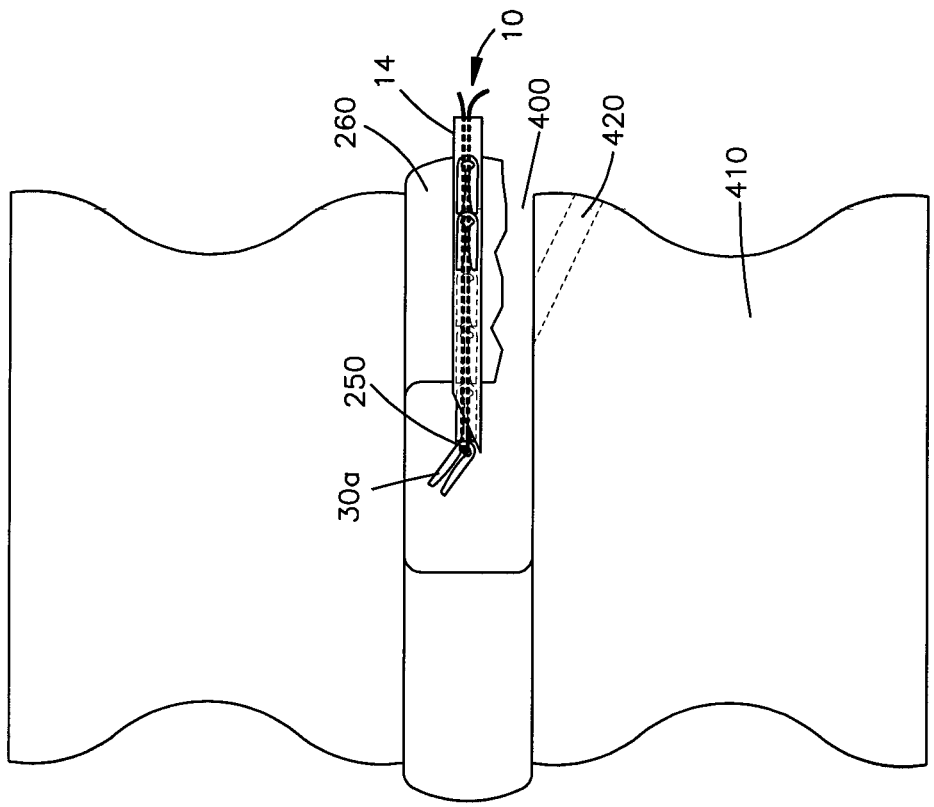
FIG. 13B is a side view of the soft tissue defect repair system of FIG. 1A being advanced through soft tissue and ejecting a first suture anchor.
Figure 13A:
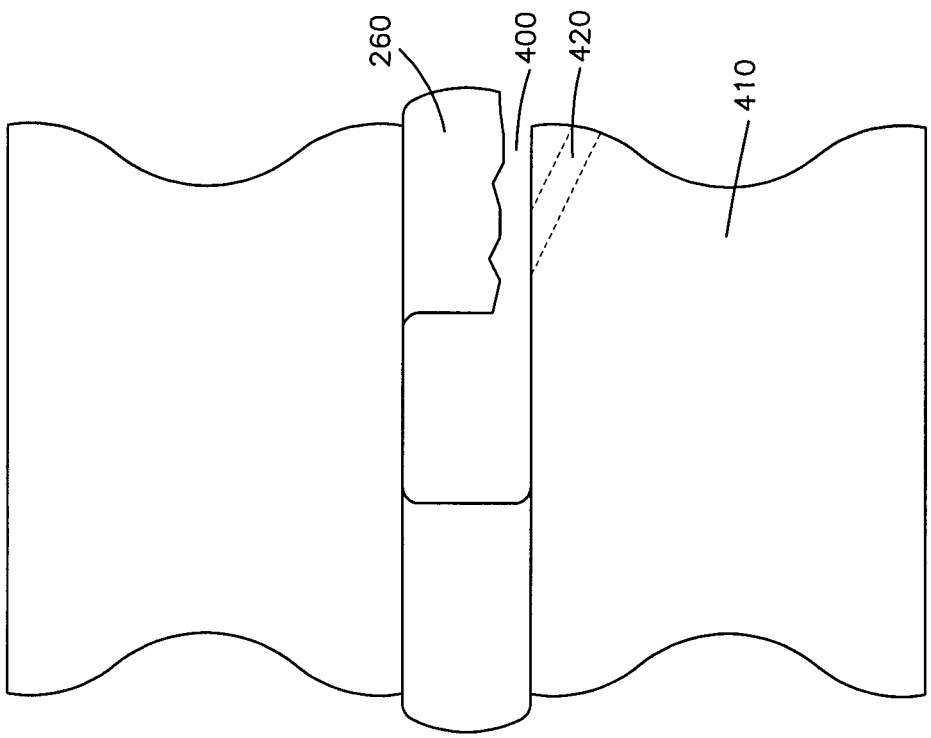
FIG. 13A is a side view of a soft tissue defect adjacent to a bony element.

Referring to FIGS. 13A-13D, the soft tissue defect repair system 10 may be used to repair a soft tissue defect 400 near or adjacent to a bony element 410, the example of which that is shown in FIG. 13A being an annulus rim tear. Such a method or procedure may begin with the formation of a transosseous tunnel 420 as shown in FIG. 13A. Once formed, the soft tissue defect repair system 10 and in particular the needle 14 is advanced through the full thickness of the soft tissue from the first side of the tissue to the second side of the tissue on the side of the defect 400 opposite the bony element 410 as shown in FIG. 13B.

The first anchor 30a is then deployed on the second side of the tissue, thereby capturing the suture 250 and locking the suture 250 in place. The needle 14 is then retracted to the first side of the tissue and moved adjacent the pre-formed transosseous tunnel 420, where the needle 14 is then passed through the transosseous tunnel 420, as shown in FIG. 13C. The suture 250 is then drawn in tension to reapproximate the tissue to the bony element and the second anchor 30b is deployed on the second side of the bony element 410, thereby locking the suture 250 in place while simultaneously anchoring on the second side of the bony element 410, as shown in FIG. 13D. The method steps can be repeated until a desired approximation of the defect 400 is achieved. A plurality of preformed transosseous tunnels 410 may be utilized. It should be understood, however, that the first anchor 30a may be deployed through the transosseous tunnel 410 and the second anchor 30b may be deployed through the soft tissue. It should be understood that in embodiments where the anchor includes a capturing cleat, both the first and second anchors are ejected and then the tissue is approximated, and that in embodiments where the anchor includes a locking cleat, the tissue is approximated prior to the second anchor being ejected.

Figure 14C:
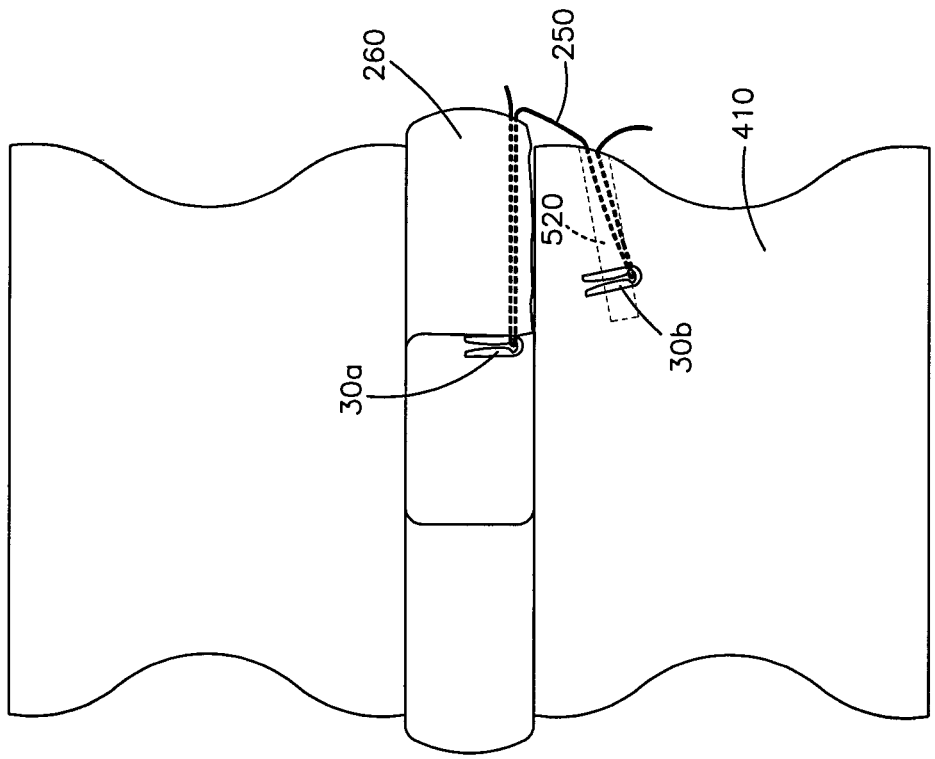
FIG. 14C is a side view of the soft tissue defect repair system of FIG. 15B being advanced through a transosseous tunnel of the bony element, and ejecting a second suture anchor.
Figure 14D:
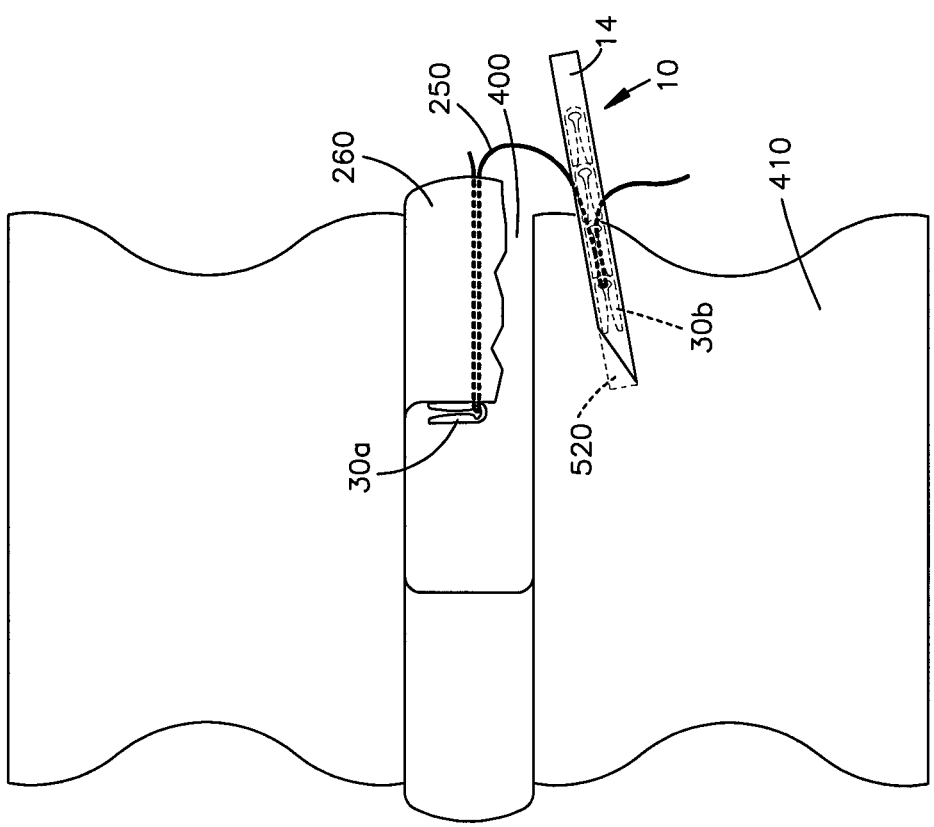
FIG. 14D is a side view of the soft tissue defect after it has been approximated.

In reference to FIGS. 14A-14D, an alternate method of implementing the soft tissue defect repair system 10 is illustrated. Similar to the method described in reference to FIGS. 13A-13D, the method shown in FIGS. 14A-14D is used to repair a soft tissue defect 400 near or adjacent a bony element 410, such as an annulus rim tear. As shown, the method or procedure begins with the formation of a transosseous tunnel 520 that terminates within the bony element 410, as opposed to the transosseous tunnel 420, which extends out of the bony element. As shown in FIG. 14B the soft tissue defect repair system 10, and in particular the needle 14 is advanced through the full thickness of soft tissue from the first side of the tissue to the second side of the tissue on the side of the defect 400 opposite the bony element.

The first anchor 30a is then deployed on the second side of the tissue, thereby capturing the suture 250 and locking the suture 250 in place. The system 10 and in particular the needle 14 is then retracted to the first side of the tissue and moved adjacent the pre-formed transosseous tunnel 520, where the system 10 and in particular the needle 14 is then passed into, but not through, the transosseous tunnel 520, as shown in FIG.

14C. The suture 250 is then drawn into tension to reapproximate the tissue to the bony element 410 and the second anchor 30b is ejected and anchored within the interior of the transosseous tunnel 520, thereby locking the suture 250 in place. In the illustrated embodiment, the second anchor 30b may assume the form of a toggling bone anchor or a double ended anchor to allow it to be deployed and optimally anchored, i.e., at more than one point, within the interior of the transosseous tunnel 520. A plurality of preformed transosseous tunnels 410 may be utilized. The method steps are repeated until a desired approximation of the defect 400 is achieved. It should be understood that in embodiments where the anchor includes a capturing cleat, both the first and second anchors are ejected and then the tissue is approximated, and that in embodiments where the anchor includes a locking cleat, the tissue is approximated prior to the second anchor being ejected.

A threaded or press-fit cannulated cylindrical implant (not shown) can optionally be utilized by inserting the cannulated cylindrical implant into the transosseous tunnel 420 or 520 to shield the bony element from the forces imparted to it by the suture 250 or anchors 30a-30n. The cannulated cylindrical implant is sized and configured to extend the entire length of the transosseous tunnel 420 or 520 so as to achieve bicortical purchase and, in one embodiment, is embodied by a cannulated allograft bone dowel. In one embodiment, the cannulated cylindrical implant includes one or more tapered ends to accommodate different approach angles.

Further, a plug type component can optionally be included to fill the soft tissue defect, and can be especially useful when the defect is too large to allow the desired approximation. Such a plug is preferably formed from a compliant biomaterial, such as collagen, cellulose, hydrogels, polyurethanes, polyesters, etc., and acts as a scaffold to facilitate healing of the defect. In one embodiment, such a plug is encircled by the suture 250 and anchor 30 and is constructed to allow the tissue to be cinched around the plug, thereby providing a mechanical barrier. The plug can be attached to the suture 250 and anchor 30 construct either directly or indirectly or by using additional coupling elements, such as bridging sutures.

The methods and procedures disclosed may also implement the use of a surface patch to provide additional reinforcement to the area of weakened tissue on the first and/or second sides of the tissue. In a preferred embodiment, the patch is made of a durable biomaterial resistant to suture tear-through and conducive to tissue ingrowth, including but not limited to acellular dermis, woven PEEK fibers, or woven UHMWPE fibers. The surface patch may also be used to reduce tissue laxity or reduce tissue bulging where there may or may not be a defect present, such as annulus bulging related to a focal or broad-based annulus protrusion.

Any or all of the elements previously described can be radiopaque to enable intra- and post-operative visualization via radiographic imaging. Additionally, any of the above embodiments may employ multiple soft tissue repair systems to repair a single defect.

Any of the soft tissue defect repair systems disclosed may be provided as a kit. For example, a system that includes a needle, a sheath, and a push rod may be provided as a kit, either by themselves or with strands of suture, and/or suture anchors.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

What is claimed:

1. A soft tissue repair system comprising:
a needle including a needle body and a tip that extends from the needle body, the needle body defining an elongate channel that is configured to house at least one suture anchor, a suture anchor ejection port, and a transverse opening disposed adjacent the ejection port, the transverse opening configured to receive a strand of suture that extends transverse across and entirely through the needle body with respect to the elongate channel;
a sheath having a sheath body that is movable relative to the needle between a first position and a second position, the sheath body defining a transverse opening extending from a first outer side sheath surface of the sheath to a second outer side sheath surface of the sheath that is located on an opposite side surface of the sheath from the first outer side sheath surface and that is aligned with the transverse opening of the needle body such that the transverse openings, in combination, define an enclosed suture through hole that extends across and through both the needle body and the sheath body such that the strand of suture can extend from outside the first outer side sheath surface across the sheath and needle to outside the second outer side sheath surface at least substantially perpendicular to the elongated channel of the needle when the sheath is in the first position, the suture through hole being configured to surround the strand of suture so as to retain the strand of suture, wherein movement of the sheath from the first position to the second position moves the transverse opening of the sheath out of alignment with the transverse opening of the needle to thereby expose the transverse opening of the needle through which the suture strand is removable from the needle; and
an actuator configured to move relative to the needle so as to push the suture anchor from the elongate channel past the suture through hole when the sheath is in the first position, and toward the ejection port, such that the suture anchor engages the suture strand as it passes the suture through hole, and carries the suture strand as it is subsequently ejected from the needle out the ejection port.

2. The soft tissue repair system of claim 1, further comprising a plurality of suture anchors stacked within the needle channel.

3. The soft tissue repair system of claim 2, wherein each suture anchor includes a proximal tongue that is configured to be engaged by a distal end of the actuator.

4. The soft tissue repair system of claim 2, wherein each suture anchor is a wire coil made from a shape memory material.

5. The soft tissue repair system of claim 2, wherein each suture anchor includes a distal cleat that is configured to engage the suture strand.

6. The soft tissue repair system of claim 5, wherein each suture anchor includes a proximal cleat.

7. The soft tissue repair system of claim 5, wherein the cleat is a locking cleat.

8. The soft tissue repair system of claim 1, wherein the sheath is configured to translate proximally with respect to the needle from the first position to the second position.

9. The soft tissue repair system of claim 8, wherein the suture strand is released when the sheath is translated to the second position.

10. The soft tissue repair system of claim 8, wherein the sheath body defines a slot that is configured to allow the suture anchor to pass therethrough.

11. The soft tissue repair system of claim 1, further comprising a strand of suture.

12. A soft tissue repair system configured to retain a plurality of anchors and individually eject at least a first anchor of the plurality of anchors, the soft tissue repair system comprising:
- a needle having a needle body that is elongate in a longitudinal direction and a tip that extends from the needle body, the needle body defining 1) a retention channel that extends along the longitudinal direction and is configured to retain the plurality of suture anchors, 2) an ejection port that extends into the needle body along a first direction transverse to the longitudinal direction at a location adjacent to the retention channel, and 3) a transverse opening that extends into the needle body along a second direction transverse to the longitudinal direction, the transverse opening disposed between the retention channel and the ejection port, the transverse opening configured to receive a suture strand;
- a sheath configured to be disposed coaxially around the exterior of the needle body, and translatable with respect to the needle body between a first position in which the sheath cooperates with the needle to retain the suture strand to the needle, and a second position in which the suture strand is released from the needle, the sheath including a sheath body that defines a slot that extends into the sheath body along the first direction whereby the slot and ejection port align when the sheath is in the first position so as to define an ejection path out the needle and sheath; and
- an actuator configured to move the first anchor from the elongate channel, past the suture through hole, and to the ejection port, such that the first anchor engages the suture strand as the first anchor passes the transverse opening and carries the suture strand as the first anchor is ejected from the ejection port and slot along the ejection path.

13. The soft tissue repair system of claim 12, wherein the ejection port is proximal to the tip.

14. The soft tissue repair system of claim 12, wherein the actuator is a pusher rod.

15. The soft tissue repair system of claim 12, wherein the tip is conical.

16. The soft tissue repair system of claim 12, wherein the tip is an awl tip.

17. The soft tissue repair system of claim 12, wherein (i) the sheath body defines a transverse opening that extends transversely through the sheath body, and (ii) the transverse openings of the sheath body and the needle body are configured to align to thereby define a suture through hole.

18. The soft tissue repair system of claim 12, wherein a distal end of the actuator defines a recess configured to engage a proximal end of one of the suture anchors of the plurality of anchors.

19. The soft tissue repair system of claim 12, further comprising the plurality of suture anchors stacked within the needle channel.

20. The soft tissue repair system of claim 19, wherein each suture anchor includes a distal cleat that is configured to engage the suture strand.

21. The soft tissue repair system of claim 19, wherein each suture anchor includes a proximal cleat.

22. The soft tissue repair system of claim 19, wherein each suture anchor includes a proximal tongue that is configured to be engaged by a distal end of the actuator.

23. The soft tissue repair system of claim 19, wherein each suture anchor is a wire coil made from a shape memory material.

24. The soft tissue repair system of claim 12, further comprising a strand of suture.

25. The soft tissue repair system of claim 12, wherein the transverse opening is configured to hold the strand of suture such that the strand of suture is perpendicular to the longitudinal direction.

26. The soft tissue repair system of claim 12, wherein the first direction and second direction are parallel.

27. A soft tissue repair system configured to retain a plurality of anchors and individually eject at least a first anchor of the plurality of anchors, the soft tissue repair system comprising:
- a needle having a needle body that defines a proximal end and a distal end spaced from the proximal end along a longitudinal direction, the needle further having a tip that extends from a distal end of the needle body, the needle body including a wall that defines 1) a retention channel that extends along the longitudinal direction, the retention channel being configured to retain the plurality of anchors, 2) a transverse ejection port, and 3) a transverse opening that is disposed between the retention channel and the ejection port, the transverse opening being configured to receive a suture strand, wherein the wall includes an angled portion that extends distally from the transverse opening, the wall being configured to release the suture strand from the transverse opening;
- an actuator configured to move the first anchor from the elongate channel, past the transverse opening and to the ejection port, such that the first anchor engages the suture strand as the first anchor passes the transverse opening and the suture strand disengages from the transverse opening along the angled portion as the first anchor is ejected from the ejection port; and
- a sheath configured to be disposed coaxially around the exterior of the needle body, and translatable with respect to the needle body between a first position in which the sheath cooperates with the needle to retain the suture strand to the needle, and a second position in which the suture strand is released from the needle, the sheath including a sheath body that defines a slot that extends into the sheath body whereby the slot and ejection port align when the sheath is in the first position so as to define an ejection path out the needle and sheath.

28. The soft tissue repair system of claim 27, wherein (i) the sheath body defines a transverse opening and (ii) the transverse openings of the sheath body and the needle body are configured to align to thereby define a suture through hole.

29. The soft tissue repair system of claim 27, further comprising the plurality of suture anchors stacked within the needle channel.

* * * * *